US010651659B2

(12) United States Patent
Zeine et al.

(10) Patent No.: US 10,651,659 B2
(45) Date of Patent: May 12, 2020

(54) TECHNIQUES FOR REDUCING HUMAN EXPOSURE TO WIRELESS ENERGY IN WIRELESS POWER DELIVERY ENVIRONMENTS

(71) Applicant: Ossia Inc., Bellevue, WA (US)

(72) Inventors: Hatem Ibrahim Zeine, Bellevue, WA (US); Siamak Ebadi, Bellevue, WA (US); Alireza Pourghorban Saghati, Los Gatos, CA (US); Anas Alfarra, Bellevue, WA (US); Douglas Williams, Seattle, WA (US)

(73) Assignee: Ossia Inc., Bellevue, WA (US)

(*) Notice: Subject to any disclaimer, the term of this patent is extended or adjusted under 35 U.S.C. 154(b) by 0 days.

(21) Appl. No.: 16/243,611

(22) Filed: Jan. 9, 2019

(65) Prior Publication Data

US 2019/0148950 A1 May 16, 2019

Related U.S. Application Data

(63) Continuation of application No. 15/881,983, filed on Jan. 29, 2018, now Pat. No. 10,181,730, which is a continuation of application No. 14/988,010, filed on Jan. 5, 2016, now Pat. No. 9,882,398.

(60) Provisional application No. 62/100,007, filed on Jan. 5, 2015.

(51) Int. Cl.
| | |
|---|---|
| *H04B 1/3827* | (2015.01) |
| *H02J 5/00* | (2016.01) |
| *H02J 50/10* | (2016.01) |
| *H02J 50/90* | (2016.01) |
| *H02J 50/60* | (2016.01) |

(52) U.S. Cl.
CPC ............. *H02J 5/005* (2013.01); *H02J 50/10* (2016.02); *H02J 50/60* (2016.02); *H02J 50/90* (2016.02)

(58) Field of Classification Search
CPC ............................... H02J 7/025; H04B 1/3838
USPC ..................... 307/104; 455/411, 438, 41.1
See application file for complete search history.

(56) References Cited

U.S. PATENT DOCUMENTS

| 10,181,730 | B2* | 1/2019 | Zeine | ............ H02J 50/60 |
|---|---|---|---|---|
| 2002/0183882 | A1* | 12/2002 | Dearing | ....... G06K 7/10336 |
| | | | | 700/115 |
| 2008/0228062 | A1* | 9/2008 | Zwirn | ............ A61B 5/0046 |
| | | | | 600/407 |
| 2010/0069744 | A1* | 3/2010 | Simpkin | ........... A61B 5/0507 |
| | | | | 600/425 |
| 2011/0304512 | A1 | 12/2011 | Friederich et al. | |
| 2012/0050109 | A1* | 3/2012 | Nysen | .............. H01Q 1/243 |
| | | | | 343/700 MS |

(Continued)

FOREIGN PATENT DOCUMENTS

WO   WO 2014194455 A1   12/2014

*Primary Examiner* — Adam D Houston

(57) ABSTRACT

Embodiments of the present disclosure describe techniques for reducing human exposure to wireless energy in wireless power delivery environments. In some embodiments, a wireless power reception apparatus configured to receive wireless power from a wireless charging system in a wireless power delivery environment is disclosed. The wireless power reception apparatus includes a control system and an antenna array. In some embodiments, the control system is configured to dynamically adjust transmission and reception radiation patterns of the antenna array to reduce human exposure to wireless radio frequency (RF) energy.

20 Claims, 19 Drawing Sheets

(56) References Cited

U.S. PATENT DOCUMENTS

| | | | |
|---|---|---|---|
| 2012/0094594 A1 | 4/2012 | Rofougaran et al. | |
| 2012/0129535 A1 | 5/2012 | Oh et al. | |
| 2012/0142286 A1 | 6/2012 | Mitomo et al. | |
| 2012/0208554 A1 | 8/2012 | Won et al. | |
| 2013/0135137 A1* | 5/2013 | Mulder | A61B 5/113 342/28 |
| 2013/0163705 A1* | 6/2013 | Stirland | H01Q 3/26 375/346 |
| 2013/0237272 A1 | 9/2013 | Prasad | |
| 2014/0128032 A1* | 5/2014 | Muthukumar | H01Q 3/00 455/411 |
| 2014/0375501 A1 | 12/2014 | Nikitin | |
| 2016/0197522 A1* | 7/2016 | Zeine | H02J 5/005 307/104 |
| 2017/0054840 A1* | 2/2017 | Kobayashi | H04B 1/385 |
| 2017/0093229 A1* | 3/2017 | Sindia | H02J 50/12 |
| 2017/0110888 A1* | 4/2017 | Leabman | H02J 5/005 |
| 2017/0134131 A1* | 5/2017 | Sharma | H04B 7/0617 |
| 2017/0181105 A1* | 6/2017 | John | H04W 52/283 |
| 2017/0184437 A1* | 6/2017 | Welle | G01F 23/284 |
| 2017/0194996 A1* | 7/2017 | Shi | H04B 1/3838 |
| 2017/0222678 A1* | 8/2017 | Abreu | H04M 1/0249 |
| 2017/0230123 A1* | 8/2017 | Lagnado | H04B 17/102 |
| 2017/0290011 A1* | 10/2017 | Kushnir | G01S 7/006 |
| 2017/0338550 A1* | 11/2017 | Alon | H04B 17/102 |
| 2019/0356349 A1* | 11/2019 | Lan | G01R 29/0814 |

\* cited by examiner ically adjust the cumulative radiation pattern of the multiple antennas based on the orientation of the multiple antennas relative to the user of the electronic device.

TECHNIQUES FOR REDUCING HUMAN EXPOSURE TO WIRELESS ENERGY IN WIRELESS POWER DELIVERY ENVIRONMENTS

CROSS-REFERENCE TO RELATED APPLICATIONS

This application is a continuation of U.S. patent application Ser. No. 15/881,983 titled "TECHNIQUES FOR REDUCING HUMAN EXPOSURE TO WIRELESS ENERGY IN WIRELESS POWER DELIVERY ENVIRONMENTS" filed on Jan. 29, 2018, now allowed; which is a continuation of U.S. patent application Ser. No. 14/988,010 titled "TECHNIQUES FOR REDUCING HUMAN EXPOSURE TO WIRELESS ENERGY IN WIRELESS POWER DELIVERY ENVIRONMENTS" filed on Jan. 5, 2016, and issued on Jan. 30, 2018, as U.S. Pat. No. 9,882,398; which claims priority to and benefit from U.S. Provisional Patent Application No. 62/100,007 titled "TECHNIQUES FOR REDUCING SPECIAL ABSORPTION RATE LEVELS FOR WIRELESSLY POWERED DEVICES" filed on Jan. 5, 2015, all of which are expressly incorporated by reference herein.

TECHNICAL FIELD

The technology described herein relates generally to the field of wireless power delivery and, more particularly, to techniques for reducing human exposure to wireless energy in wireless power delivery environments.

BACKGROUND

Delivering power wirelessly, e.g., via radio frequency (RF), to electronic devices within close proximity to the human flesh can raise safety concerns due to the potential for absorption of the RF energy by the human flesh. The Federal Communications Commission (FCC) currently limits the exposure or Special Absorption Rate (SAR) to 1.6 mW/cm$^3$ for frequencies above 1 GHz. Staying below this limit is achievable by most wireless devices that primarily transmit and receive data communications. However, this limit can be easily reached or exceeded in environments wherein wireless power is delivered.

Accordingly, a need exists for technology that overcomes the problem demonstrated above, as well as one that provides additional benefits. The examples provided herein of some prior or related systems and their associated limitations are intended to be illustrative and not exclusive. Other limitations of existing or prior systems will become apparent to those of skill in the art upon reading the following Detailed Description.

OVERVIEW

Provided herein are systems, methods, and software that facilitate various reduction of human exposure to wireless energy in wireless power delivery environments. In some embodiments, a wireless power reception apparatus is disclosed having multiple antennas and a control system. The control system is configured to dynamically adjust a cumulative radiation pattern of the multiple antennas to reduce radio frequency (RF) exposure to a user of an electronic device in which the wireless power reception apparatus is embedded. The wireless power reception apparatus is further configured to receive wireless power from a wireless power delivery system in a wireless power delivery environment and to provide the power to the electronic device.

In some embodiments, the wireless power reception apparatus dynamically adjusts the cumulative radiation pattern of the multiple antennas by controlling a direction and intensity of a beacon signal transmitted by the multiple antennas.

In some embodiments, the wireless power reception apparatus dynamically adjusts the cumulative radiation pattern of the multiple antennas by controlling an angle of incidence of the wireless power received from the wireless power delivery system.

In some embodiments, the multiple antennas each have corresponding radiation patterns that are controlled over amplitude and phase by the control system. In some embodiments, the radiation patterns of the multiple antennas collectively comprise the cumulative radiation pattern.

In some embodiments, the control system is further configured to detect an orientation of the multiple antennas relative to the user of the electronic device and to dynamically adjust the cumulative radiation pattern of the multiple antennas based on the orientation of the multiple antennas relative to the user of the electronic device.

In some embodiments, the control system is further configured to detect a full or partial blockage of one or more of the multiple antennas and to dynamically adjust the cumulative radiation pattern of the multiple antennas based on the full or partial blockage of the one or more of the multiple antennas.

In some embodiments, the control system is preconfigured with a set of fixed cumulative radiation patterns, and the control system is configured to cycle through the set of fixed cumulative radiation patterns to identify an optimal antenna configuration for reducing RF exposure to the user of an electronic device.

In some embodiments, the control system is configured to dynamically adjust the cumulative radiation pattern in a direction away from the user of the electronic device.

In some embodiments, the multiple antennas are configured to have the same resonance frequency.

In some embodiments, an electronic device is disclosed having electronic components including one or more processors, multiple antennas disposed on or within the electronic device, and a computer-readable storage medium. The computer-readable storage medium has instructions stored thereon which, when executed by the one or more processors, direct the electronic device to dynamically adjust a cumulative radiation pattern of the multiple antennas to reduce radio frequency (RF) exposure to a user of an electronic device in which the wireless power reception apparatus is embedded. The multiple antennas each have a corresponding radiation pattern that is controlled over amplitude and phase, the radiation patterns collectively comprising the cumulative radiation pattern. The wireless power reception apparatus is configured to receive wireless power from a wireless power delivery system in a wireless power delivery environment and to provide the power to the electronic device.

In some embodiments, the electronic device dynamically adjusts the cumulative radiation pattern of the multiple antennas by controlling a direction and intensity of a beacon signal transmitted by the multiple antennas or directing an angle of incidence of the wireless power received from the wireless power delivery system.

In some embodiments, the instructions, when executed by the one or more processors, further direct the electronic device to detect an orientation of the multiple antennas relative to the user of the electronic device and dynamically adjust the cumulative radiation pattern based on the orientation of the multiple antennas relative to the user of the electronic device.

In some embodiments, the instructions, when executed by the one or more processors, further direct the electronic device to detect a full or partial blockage of one or more of the multiple antennas by the user of the electronic device and dynamically adjust the cumulative radiation pattern based on the full or partial blockage.

In some embodiments, the instructions, when executed by the one or more processors, further direct the electronic device to cycle through a set of fixed cumulative radiation patterns to identify an optimal antenna configuration for reducing RF exposure to the user of an electronic device. The control system is preconfigured with the set of fixed cumulative radiation patterns.

In some embodiments, the instructions, when executed by the one or more processors, direct the electronic device to dynamically adjust the cumulative radiation pattern in a direction away from the user of the electronic device.

In some embodiments, a method of operating a wireless power reception apparatus to reduce radio frequency (RF) exposure to a user of an electronic device in which the wireless power reception apparatus is embedded is disclosed. The method includes detecting an orientation of an antenna array of the wireless power reception apparatus relative to a user of the electronic device and adjusting a cumulative radiation pattern of the antenna array to reduce the RF exposure to the user of an electronic device. Each antenna of the antenna array has a corresponding radiation pattern that is controlled over amplitude and phase, the radiation patterns collectively comprise the cumulative radiation pattern. The wireless power reception apparatus is configured to receive wireless power from a wireless power delivery system in a wireless power delivery environment and to provide the power to the electronic device.

In some embodiments, the method further includes detecting the orientation of the antenna array of the wireless power reception apparatus relative to the user of the electronic device comprises identifying a full or partial blockage of one or more antennas of the antenna array by the user of the electronic device.

This Overview is provided to introduce a selection of concepts in a simplified form that are further described below in the Technical Disclosure. It may be understood that this Overview is not intended to identify key features or essential features of the claimed subject matter, nor is it intended to be used to limit the scope of the claimed subject matter.

BRIEF DESCRIPTION OF THE DRAWINGS

One or more embodiments of the present invention are illustrated by way of example and not limitation in the figures of the accompanying drawings, in which like references indicate similar elements.

DETAILED DESCRIPTION

Figure 1:
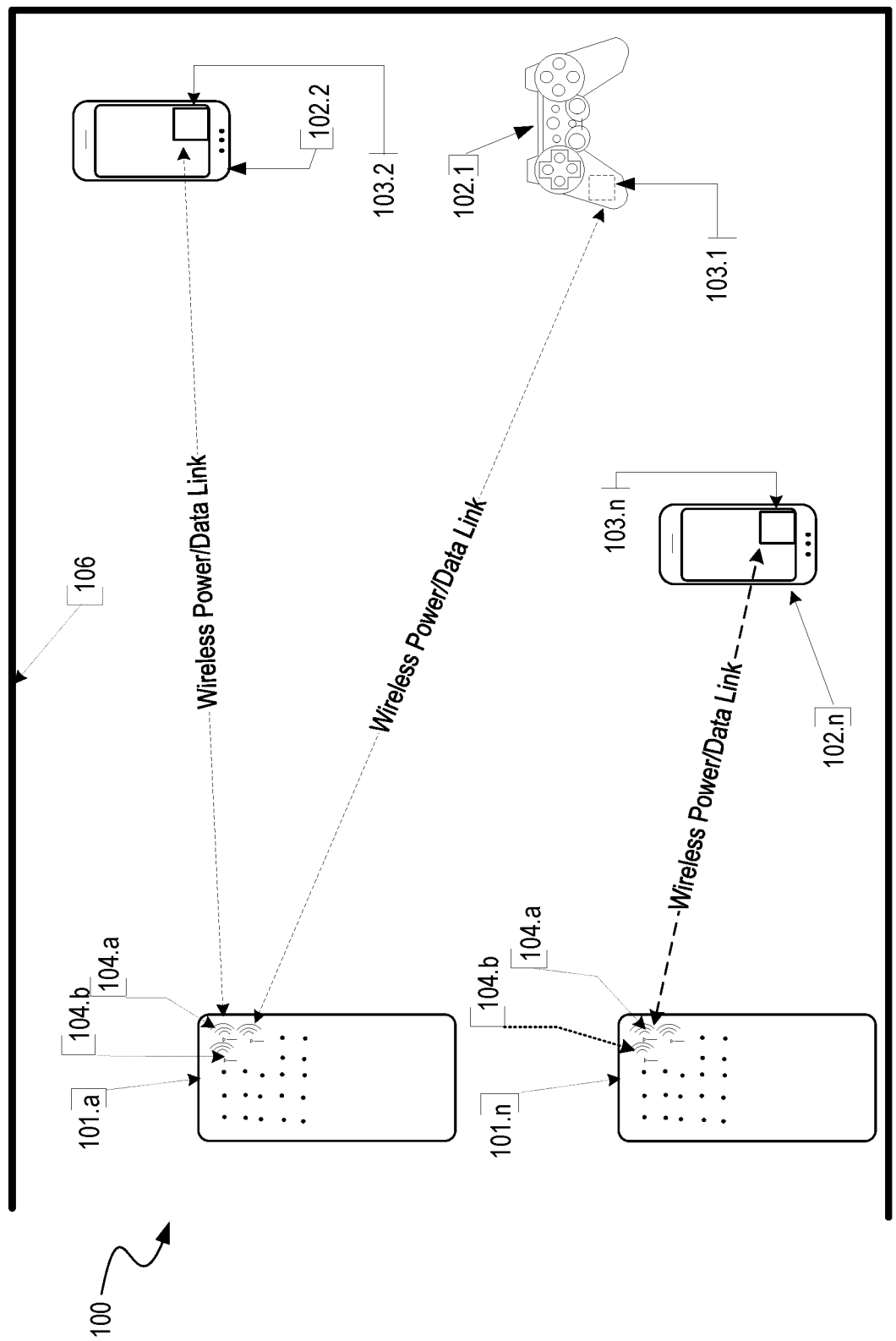
FIG. 1 depicts a diagram illustrating example components of a wireless power delivery environment in accordance with some embodiments.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but no other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

Embodiments of the present disclosure describe techniques for reducing human exposure to wireless energy in wireless power delivery environments.

I. Wireless Power Delivery System Overview/Architecture

FIG. 1 is a diagram illustrating example components of a wireless power delivery environment 100. More specifically, FIG. 1 illustrates an example wireless power delivery environment 100 in which wireless power and/or data can be delivered from one or more wireless chargers 101 to wireless devices 102.1-102.$n$ having one or more power receiver clients 103.1-103.$n$ (also referred to herein as "wireless power receivers" or "wireless power clients"). The wireless power receivers are configured to receive and/or otherwise harvest the wireless power transmitted by the one or more wireless chargers 101 and provide the received wireless power to the corresponding wireless device 102.1-102.$n$.

As shown in the example of FIG. 1, the wireless devices 102.1-102.$n$ are mobile phone devices 102.2 and 102.$n$, respectively, and a wireless game controller 102.1, although the wireless devices 102.1-102.$n$ can be any (smart or dumb, mobile or static) device or system that needs power and is capable of receiving wireless power via one or more integrated power receiver clients 103.1-103.$n$. As discussed herein, the one or more integrated power receiver clients or "wireless power receivers" receive and process power from one or more transmitters/chargers 101.$a$-101.$n$ and provide the power to the wireless devices 102.1-102.$n$ for operation thereof.

Each charger 101 (also referred to herein as a "transmitter", "array of antennas" or "antenna array system") can include multiple antennas 104, e.g., an antenna array including hundreds or thousands of antennas, which are capable of delivering wireless power to wireless devices 102. In some embodiments, the antennas are adaptively-phased radio frequency antennas. The charger 101 is capable of determining the appropriate phases to deliver a coherent power transmission signal to the power receiver clients 103. The array is configured to emit a signal (e.g., continuous wave or pulsed power transmission signal) from multiple antennas at a specific phase relative to each other. It is appreciated that use of the term "array" does not necessarily limit the antenna array to any specific array structure. That is, the antenna array does not need to be structured in a specific "array" form or geometry. Furthermore, as used herein he term "array" or "array system" may be used include related and peripheral circuitry for signal generation, reception and transmission, such as radios, digital logic and modems. In some embodiments, the charger 101 can have an embedded Wi-Fi hub.

The wireless devices 102 can include one or more receive power clients 103. As illustrated in the example of FIG. 1, power delivery antennas 104$a$ and data communication antennas 104$b$ are shown. The power delivery antennas 104$a$ are configured to provide delivery of wireless radio frequency power in the wireless power delivery environment. The data communication antennas are configured to send data communications to and receive data communications from the power receiver clients 103.1-103 and/or the wireless devices 102.1-102.$n$. In some embodiments, the data communication antennas can communicate via Bluetooth, Wi-Fi, ZigBee, etc.

Each power receiver client 103.1-103.$n$ includes one or more antennas (not shown) for receiving signals from the chargers 101. Likewise, each charger 101.$a$-101.$n$ includes an antenna array having one or more antennas and/or sets of antennas capable of emitting continuous wave signals at specific phases relative to each other. As discussed above, each array is capable of determining the appropriate phases for delivering coherent signals to the power receiver clients 102.1-102.$n$. For example, coherent signals can be determined by computing the complex conjugate of a received beacon signal at each antenna of the array such that the coherent signal is properly phased for the particular power receiver client that transmitted the beacon signal.

Although not illustrated, each component of the environment, e.g., wireless power receiver, charger, etc., can include control and synchronization mechanisms, e.g., a data communication synchronization module. The chargers 101.$a$-101.$n$ can be connected to a power source such as, for example, a power outlet or source connecting the chargers to a standard or primary alternating current (AC) power supply in a building. Alternatively or additionally, one or more of the chargers 101.$a$-101.$n$ can be powered by a battery or via other mechanisms.

In some embodiments, the power receiver clients 102.1-102.$n$ and/or the chargers 101.$a$-101.$n$ utilize reflective objects 106 such as, for example, walls or other RF reflective obstructions within range to transmit beacon signals and/or receive wireless power and/or data within the wireless power delivery environment. The reflective objects 106 can be utilized for multi-directional signal communication regardless of whether a blocking object is in the line of sight between the charger and the power receiver client.

As described herein, each wireless device 102.1-102.$n$ can be any system and/or device, and/or any combination of devices/systems that can establish a connection with another device, a server and/or other systems within the example environment 100. In some embodiments, the wireless devices 102.1-102.$n$ include displays or other output functionalities to present data to a user and/or input functionalities to receive data from the user. By way of example, a wireless device 102 can be, but is not limited to, a video game controller, a server desktop, a desktop computer, a computer cluster, a mobile computing device such as a notebook, a laptop computer, a handheld computer, a mobile phone, a smart phone, a PDA, a Blackberry device, a Treo, and/or an iPhone, etc. The wireless device 102 can also be any wearable device such as watches, necklaces, rings or even devices embedded on or within the customer. Other examples of a wireless device 102 include, but are not limited to, safety sensors (e.g., fire or carbon monoxide), electric toothbrushes, electronic door lock/handles, electric light switch controller, electric shavers, etc.

Although not illustrated in the example of FIG. 1, the charger 101 and the power receiver clients 103.1-103.$n$ can each include a data communication module for communication via a data channel. Alternatively or additionally, the power receiver clients 103.1-103.$n$ can direct the wireless devices 102.1-102.$n$ to communicate with the charger via existing data communications modules. Additionally, in some embodiments the beacon signal, which is primarily referred to herein as a continuous waveform, can alternatively or additionally take the form of a modulated signal.

Figure 2:
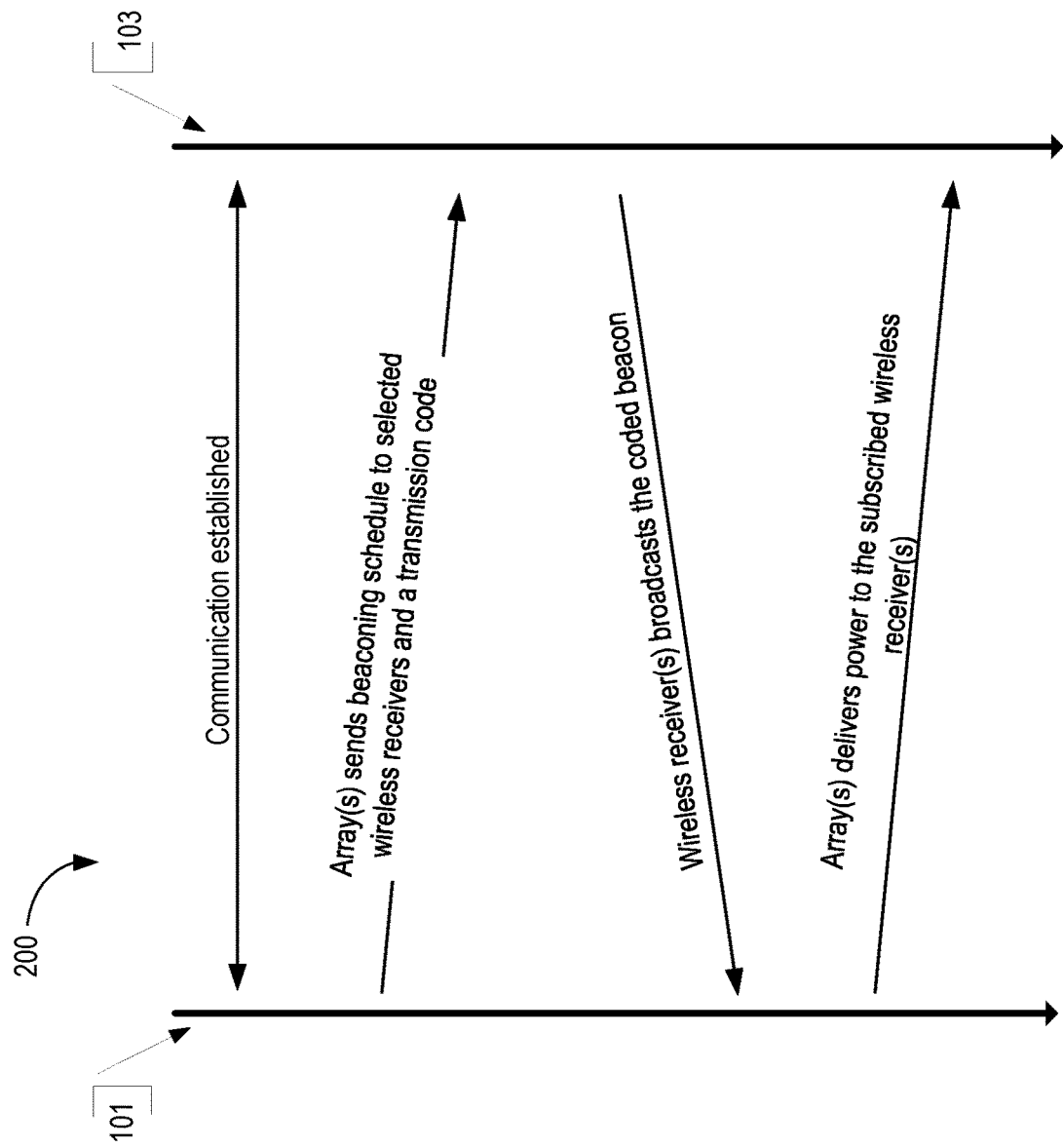
FIG. 2 depicts a sequence diagram illustrating example operations between a wireless charger and a wireless receiver device in accordance with some embodiments.

FIG. 2 is a sequence diagram 200 illustrating example operations between a wireless charger 101 and a power receiver client 103, according to an embodiment. Initially, communication is established between the charger 101 and the power receiver client 103. The charger 101 subsequently sends beacon schedule information and a transmission code to the power receiver client 103 to facilitate encoding of the beacon signal by the power receiver client 103 for subsequent isolated wireless power delivery by the charger. The charger 101 can also send power transmission scheduling information so that the power receiver client 103 knows when to expect wireless power from the charger. As discussed herein, the power receiver client 103 generates an encoded beacon signal using the transmission code and broadcasts the encoded beacon during a beacon transmission assignment indicated by the beacon schedule information, e.g., BBS cycle.

As shown, the charger 101 receives the beacon from the power receiver client 103 and decodes the encoded beacon signal using the transmission code provided to the client 103 to ensure that the client 103 is an authorized or selected client. The charger 101 also detects the phase (or direction) at which the beacon signal is received and, once the charger determines that the client is authorized, delivers wireless power and/or data to the power receiver client 103 based the phase (or direction) of the received beacon.

In some embodiments, the charger 101 determines the complex conjugate of the phase and uses the complex conjugate to deliver and/or otherwise direct or return wireless power to the power receiver client 103 via the same multiple paths over which the beacon signal is received by the charger 101. Advantageously, this technique results in isolated wireless power delivery to the power receiver client 103. As discussed herein, the precise location where the multiple paths of the isolated power delivery converge at the power receiver client 103, i.e., where the wireless energy is focused by the charger over the multiple paths, can be referred to herein as an RF energy pocket or a power ball.

As discussed below, in some embodiments, the precise location of the RF energy pocket or power ball and/or the angle of incidence of the RF energy received at the RF energy pocket or power ball can be controlled via modification to the amplitude and/or phase of an antenna array of the power receiver client 103 or the wireless device 102. Advantageously, the modification techniques reduce and/or otherwise avoid absorption of wireless energy, e.g., RF energy, by human flesh of user that is proximate to the wireless device.

In some embodiments, the charger 101 includes many antennas; one or more of which are used to deliver power to the power receiver client 103. The charger 101 can detect phases at which the beacon signals are received at each antenna. The large number of antennas may result in different coded beacon signals being received at each antenna of the charger 101. The charger may then determine the complex conjugate of the beacon signals received at each antenna. Using the complex conjugates, one or more antenna may emit a signal that takes into account the effects of the large number of antennas in the charger 101. In other words, the charger 101 emits a signal from one or more antennas in such a way as to create an aggregate signal from the one or more of the antennas that approximately recreates the waveform of the beacon in the opposite direction.

As discussed herein, wireless power can be delivered in power cycles defined by power schedule information. A more detailed example of the signaling required to commence wireless power delivery is described now with reference to FIG. 3.

Figure 3:
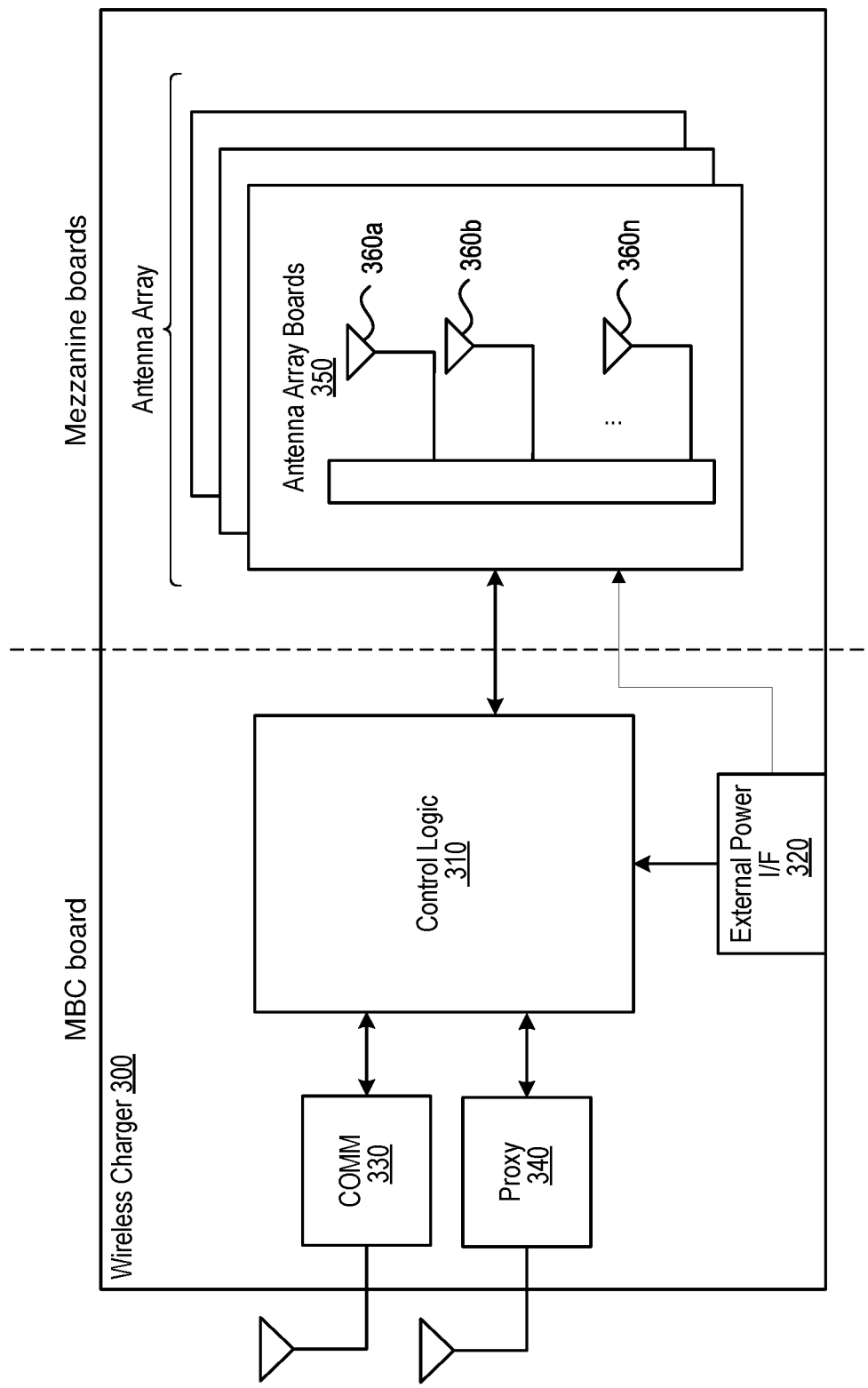
FIG. 3 depicts a block diagram illustrating example components of a wireless power transmitter (charger or wireless power delivery system) in accordance with some embodiments.

FIG. 3 is a block diagram illustrating example components of a wireless charger 300, in accordance with an embodiment. As illustrated in the example of FIG. 3, the wireless charger 300 includes a master bus controller (MBC) board and multiple mezzanine boards that collectively comprise the antenna array. The MBC includes control logic 310, an external power interface (UF) 320, a communication block 330, and proxy 340. The mezzanine (or antenna array boards 350) each include multiple antennas 360$a$-360$n$. Some or all of the components can be omitted in some embodiments. Additional components are also possible.

The control logic 310 is configured to provide control and intelligence to the array components. The control logic 310 may comprise one or more processors, FPGAs, memory units, etc., and direct and control the various data and power communications. The communication block 330 can direct data communications on a data carrier frequency, such as the base signal clock for clock synchronization. The data communications can be Bluetooth, Wi-Fi, ZigBee, etc. Likewise, the proxy 340 can communicate with clients via data communications as discussed herein. The data communications can be Bluetooth, Wi-Fi, ZigBee, etc. The external power interface 320 is configured to receive external power and provide the power to various components. In some embodiments, the external power interface 320 may be configured to receive a standard external 24 Volt power supply. Alternative configurations are also possible.

An example of a system power cycle is now described. In this example, the master bus controller (MBC), which controls the charger array, first receives power from a power source and is activated. The MBC then activates the proxy antenna elements on the charger array and the proxy antenna elements enter a default "discovery" mode to identify available wireless receiver clients within range of the charger array. When a client is found, the antenna elements on the charger array power on, enumerate, and (optionally) calibrate.

The MBC generates beacon transmission scheduling information and power transmission scheduling information during a scheduling process. The scheduling process includes selection of power receiver clients. For example, the MBC can select power receiver clients for power transmission and generate a Beacon Beat Schedule (BBS) cycle and a Power Schedule (PS) for the selected wireless power receiver clients. A graphical signaling representation of an example BBS and PS is shown and discussed in greater detail with reference to FIGS. 6 and 7. As discussed herein, the power receiver clients can be selected based on their corresponding properties and/or requirements.

In some embodiments, the MBC can also identify and/or otherwise select available clients that will have their status queried in the Client Query Table (CQT). Clients that are placed in the CQT are those on "standby", e.g., not receiving a charge. The BBS and PS are calculated based on vital information about the clients such as, for example, battery status, current activity/usage, how much longer the client has until it runs out of power, priority in terms of usage, etc.

The Proxy AE broadcasts the BBS to all clients. As discussed herein, the BBS indicates when each client should send a beacon. Likewise the PS indicates when and to which clients the array should send power to. Each client starts broadcasting its beacon and receiving power from the array per the BBS and PS. The Proxy can concurrently query the Client Query Table to check the status of other available clients. A client can only exist in the BBS or the CQT (e.g., waitlist), but not in both. In some embodiments, a limited number of clients can be served on the BBS and PS (e.g., 32). Likewise, the CQT may also be limited to a number of clients (e.g., 32). Thus, for example, if more than 64 clients are within range of the charger, some of those clients would not be active in either the BBS or CQT. The information collected in the previous step continuously and/or periodically updates the BBS cycle and/or the PS.

Figure 4:
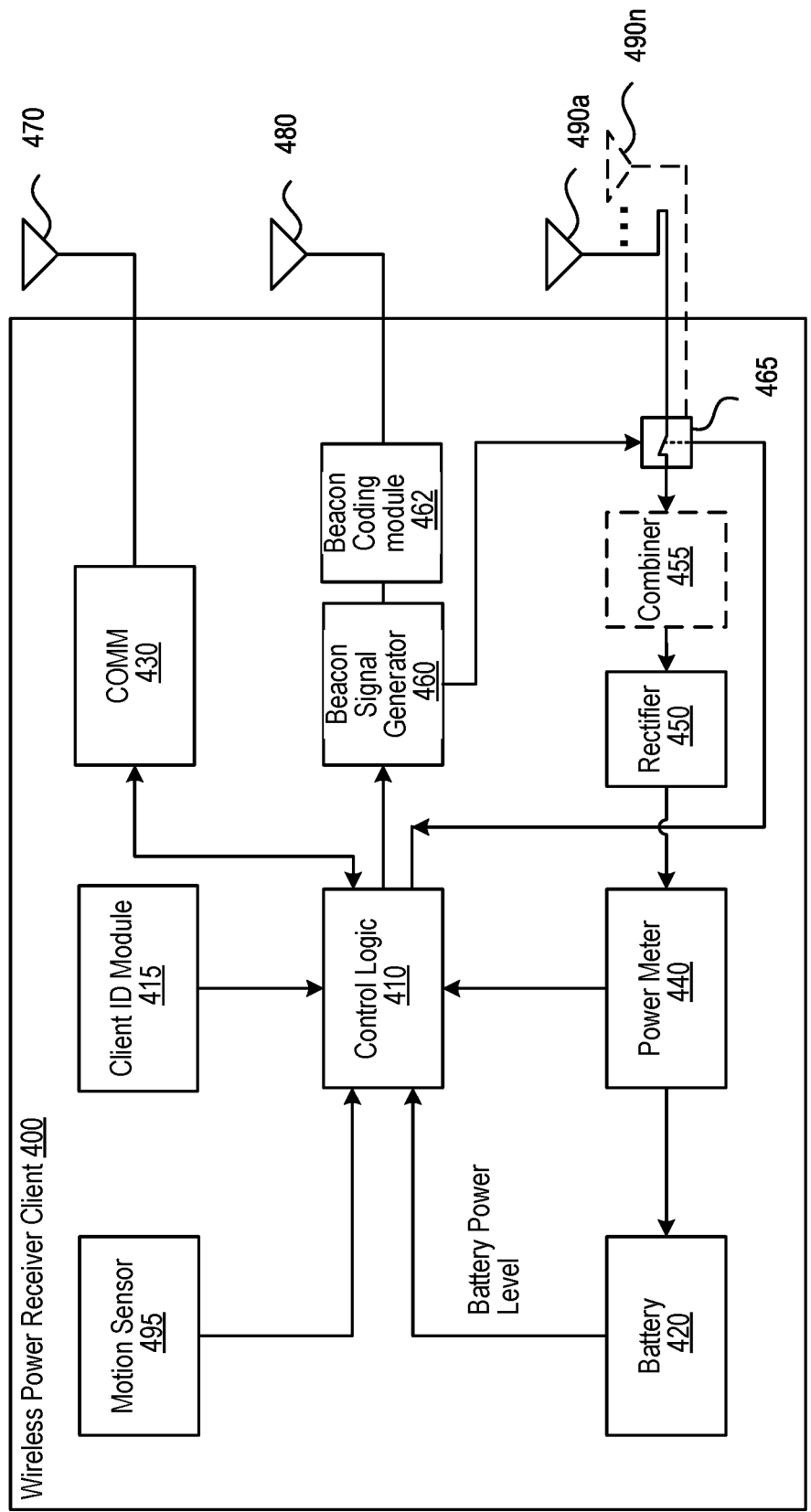
FIG. 4 depicts a block diagram illustrating example components of a wireless power receiver (client) in accordance with some embodiments.

FIG. 4 is a block diagram illustrating example components of a wireless power receiver (client), in accordance with some embodiments. As illustrated in the example of FIG. 4, the receiver 400 includes control logic 410, battery 420, communication block 430 and associated antenna 470, power meter 440, rectifier 450, a combiner 455, beacon signal generator 460, beacon coding unit 462 and an associated antenna 480, and switch 465 connecting the rectifier 450 or the beacon signal generator 460 to one or more associated antennas 490a-n. Some or all of the components can be omitted in some embodiments. For example, in some embodiments, the wireless power receiver client does not include its own antennas but instead utilizes and/or otherwise shares one or more antennas (e.g., Wi-Fi antenna) of the wireless device in which the wireless power receiver is embedded. Additional components are also possible.

A combiner 455 receives and combines the received power transmission signals from the power transmitter in the event that the receiver 400 has more than one antenna. The combiner can be any combiner or divider circuit that is configured to achieve isolation between the output ports while maintaining a matched condition. For example, the combiner 455 can be a Wilkinson Power Divider circuit. The rectifier 450 receives the combined power transmission signal from the combiner 455, if present, which is fed through the power meter 440 to the battery 420 for charging. The power meter 440 measures the received power signal strength and provides the control logic 410 with this measurement.

The control logic 410 also may receive the battery power level from the battery 420 itself. The control logic 410 may also transmit/receive via the communication block 430 a data signal on a data carrier frequency, such as the base signal clock for clock synchronization. The beacon signal generator 460 generates the beacon signal, or calibration signal, transmits the beacon signal using either the antenna 480 or 490 after the beacon signal is encoded.

It may be noted that, although the battery 420 is shown for as charged by and providing power to the receiver 400, the receiver may also receive its power directly from the rectifier 450. This may be in addition to the rectifier 450 providing charging current to the battery 420, or in lieu of providing charging. Also, it may be noted that the use of multiple antennas is one example of implementation and the structure may be reduced to one shared antenna.

In some embodiments, a client identifier (ID) module 415 stores a client ID that can uniquely identify the power receiver client in a wireless power delivery environment. For example, the ID can be transmitted to one or more chargers when communication are established. In some embodiments, power receiver clients may also be able to receive and identify other power receiver clients in a wireless power delivery environment based on the client ID.

In some embodiments, a motion sensor 495 can detect motion and signal the control logic 410 to act accordingly. For example, when a device is receiving power at high frequencies, e.g., above 500 MHz, its location may become a hotspot of (incoming) radiation. Thus, when the device is on a person, e.g., embedded in a mobile device, the level of radiation may exceed acceptable radiation levels set by the Federal Communications Commission (FCC) or other medical/industrial authorities. To avoid any potential radiation issue, the device may integrate motion detection mechanisms such as accelerometers or equivalent mechanisms. Once the device detects that it is in motion, it may be assumed that it is being handled by a user, and would trigger a signal to the array either to stop transmitting power to it, or to lower the received power to an acceptable fraction of the power. In cases where the device is used in a moving environment like a car, train or plane, the power might only be transmitted intermittently or at a reduced level unless the device is close to losing all available power.

II. Techniques for Reducing Exposure to Wireless Energy

Embodiments of the present disclosure describe techniques for reducing human exposure to wireless energy, e.g., RF energy, in wireless power delivery environments.

In some embodiments, techniques are discussed for increasing antenna aperture to reduce the human or user exposure to wireless energy in wireless power delivery environments. The aperture can be increased in a number of ways. For example, the aperture can be increased by adding additional antennas and/or by increasing the size of one or more antennas. Accordingly, in some embodiments, techniques are described to increase antenna aperture by using various previously unused surfaces of a device for additional antennas. For example, antennas can be embedded in at least a portion of the screen, e.g., glass front, of a mobile device.

Additional techniques for reducing human exposure to wireless energy, e.g., RF energy, in wireless power delivery environments are also discussed. For example, in some embodiments, techniques are disclosed for dynamically adjusting antenna transmission and reception radiation patterns to reduce human or user exposure to wireless energy, e.g., RF energy, in wireless power delivery environments. For example, an antenna transmission and reception radiation pattern can be dynamically adjusted to automatically radiate in a direction away from a user of a device to reduce SAR, e.g., RF exposure to the user.

Figure 5:
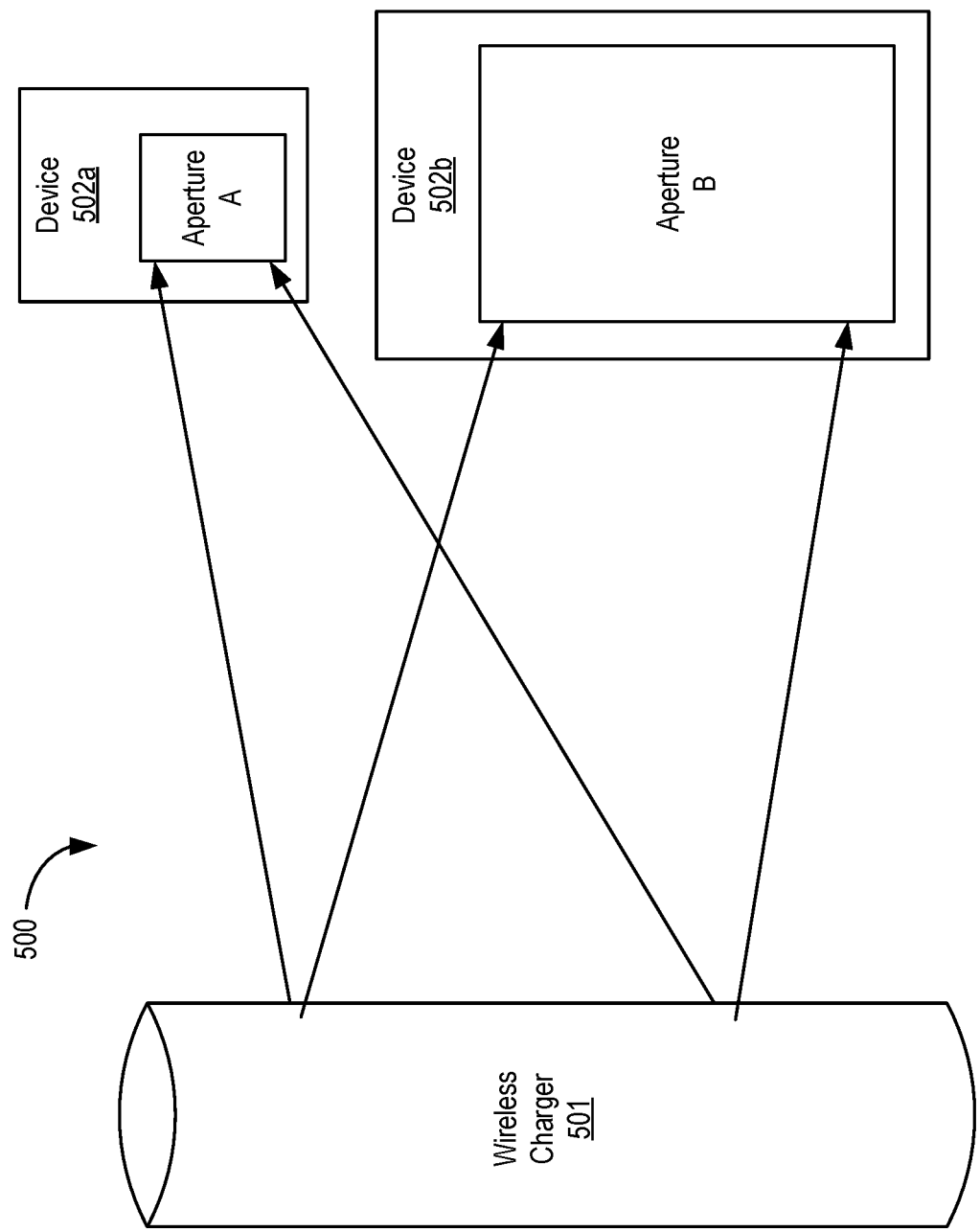
FIG. 5 depicts a diagram illustrating example components of a wireless power delivery environment 500, according to some embodiments.

FIG. 5 depicts a diagram illustrating example components of a wireless power delivery environment 500, according to some embodiments. More specifically, the example of FIG. 5 illustrates an example of how increasing the aperture of a device decreases the intensity of the electro-magnetic field or radiation pattern generated by the device if the amount of wireless power delivered to the device remains constant. As shown in the example of FIG. 5, the wireless power delivery environment includes a wireless charger 501 and devices 502a and 502b. The wireless charger 501 can be a wireless charger 101 of FIG. 1 although alternative configurations are possible. Likewise devices 502a and 502b can be wireless devices 102 of FIG. 1 although alternative configurations are possible.

As shown in the example of FIG. 5, the devices 502a and 502b include apertures A and B, respectively. An aperture is defined as the area, oriented perpendicular to the direction of an incoming radio wave, which intercepts the same amount of power from that wave as is produced by the antenna which receives the wave. Typically, the intensity of the electro-magnetic field or radiation pattern generated by a device decreases as the aperture increase.

As shown in the example of FIG. 5, aperture B is greater than aperture A. In wireless power delivery environments, a decrease in the intensity of the electro-magnetic field or radiation pattern generated by a device results in a decrease in the intensity of the electro-magnetic field and, assuming the amount of wireless power delivered to the device remains constant, reduced RF exposure to a user of the device. For example, if wireless charger 501 delivers a Watt of power to both device 502a and device 502b, the intensity of the electro-magnetic field generated around device 502b will be less than the intensity of the electro-magnetic field generated around device 502a because the energy is distributed over a larger area. More specifically, the intensity of the electro-magnetic field generated around device 502a is approximately 1/A and the intensity of the electro-magnetic field generated around device 502b is approximately 1/B.

Consequently, in some embodiments, various techniques are described for increasing an apertures on a client device. An aperture can be increased by increasing the physical size of the antenna or by introducing additional antennas or replicated antennas. As discussed above with respect to FIGS. 1-4, in some wireless power delivery environments, the wireless devices beacon the wireless charger and the wireless charger responds by delivering power in the direction in which the beacon was received. In this manner, wireless power can be delivered to a device simultaneously over multiple paths by multiple antennas in a multi-path environment.

In addition to distributing the electro-magnetic field generated around device, increasing the aperture by using multiple antennas also provides additional benefits. For example, when antennas are distributed over the available surfaces of a mobile device such as, for example, a mobile phone, one or more of the antennas may be blocked by a user of the device, e.g., a user holding the device might block one or more of the antennas from transmitting beacon signals to a charger. The charger, in turn, will not direct wireless power to the blocked antennas. In this manner, a device with multiple antennas can continue to receive wireless power directed to only the non-blocked antennas. Because the charger does not direct wireless power to the blocked antennas, the human exposure to energy, e.g., RF exposure to the user, is reduced.

As discussed above, an aperture can be increased by increasing the physical size of the antenna or by introducing additional antennas or replicated antennas. Changing the size of an antenna changes the frequency of the antenna and so, in some embodiments multiple antennas (replicated antennas) may be used so that the resonance frequency of the multiple antennas are the same or similar.

A. Dynamically Adjusting Radiation Patterns and Phased Beacon Broadcasting

Figure 6:
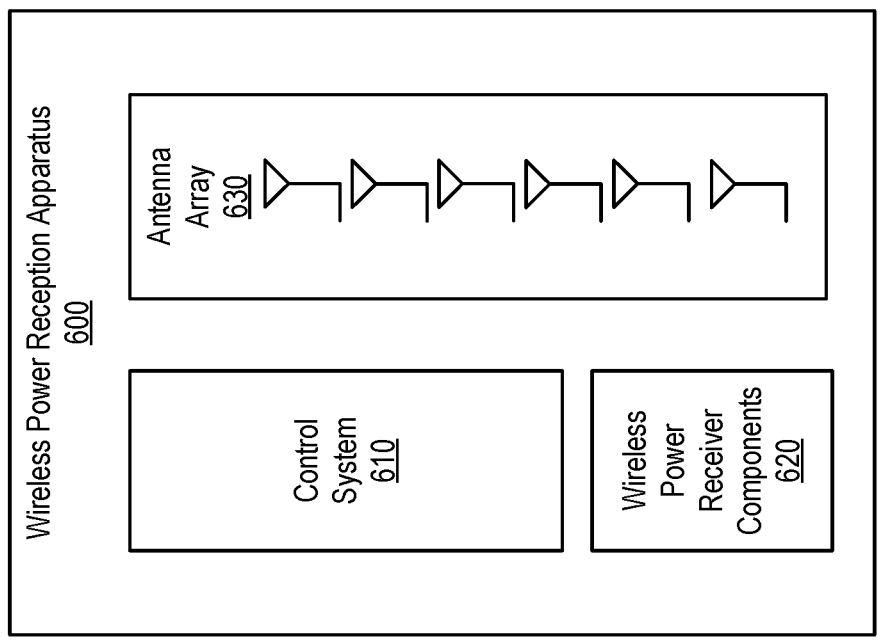
FIG. 6 depicts a diagram illustrating example components of a wireless power reception apparatus 600, according to some embodiments.

FIG. 6 depicts a diagram illustrating example components of a wireless power reception apparatus 600, according to some embodiments. As shown in the example of FIG. 6, the wireless power reception apparatus 600 includes a control system 610, one or more wireless power receiver components 620, and an antenna array 630. More or fewer components are possible. The one or more wireless power receiver components may comprise one or more components of wireless power receiver client 400 of FIG. 4. Alternatively, in some embodiments, a wireless power receiver client can include a wireless power reception apparatus.

In the example of FIG. 6, the antenna array 630 includes multiple adaptively-phased radio frequency antennas. As discussed in more detail below, each antenna can have a corresponding antenna radiation pattern that is dynamically controllable over amplitude and phase by the control system 610. The radiation patterns of the multiple antennas of the antenna array 630 collectively comprise a cumulative radiation pattern associated with the wireless power reception apparatus 600.

In some embodiments, the control system 610 can be preconfigured with a set of fixed cumulative radiation patterns, e.g., one hundred or more preconfigured amplitude and phase settings for each antenna of the antenna array 630.

Figure 7A:
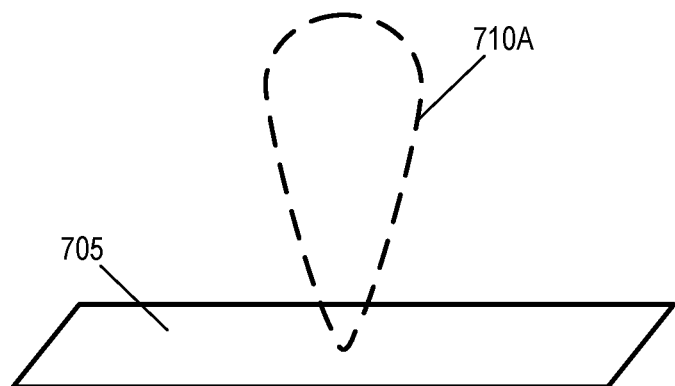
FIGS. 7A-7C depict diagrams illustrating various example antenna radiation patterns of a configurable antenna array, according to some embodiments.
Figure 7B:
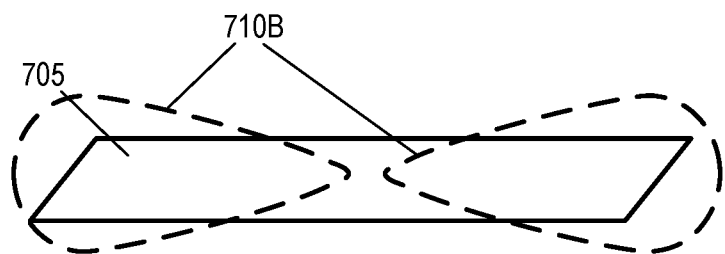
Figure 7C:
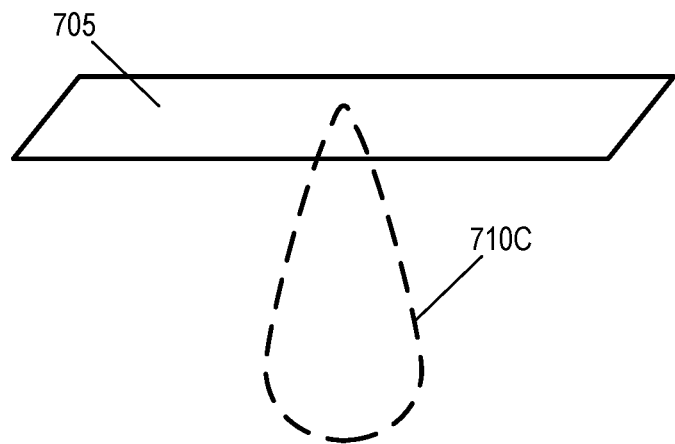

FIGS. 7A-7C depict diagrams illustrating various example antenna radiation patterns of a configurable antenna array 705, according to some embodiments. More specifically, the example of FIGS. 7A-7C illustrate various cumulative radiation patterns 710A-C of an antenna array 705 which includes multiple antennas. Although not shown in the examples of FIGS. 7A-7C, the antenna array 705 can be embedded and/or otherwise included in or with a wireless power reception apparatus and/or wireless device, e.g., wireless power reception apparatus 600 of FIG. 6. The cumulative antenna radiation patterns 710A-C are shown as examples, other radiation patterns are possible including combinations and/or variations thereof.

As discussed herein, antenna array 705 includes multiple antennas each having an antenna radiation pattern. The cumulative radiation patterns 710A-C are comprised of the radiation patterns of each of the multiple antennas of the antenna array. As will be discussed in greater detail with respect to FIG. 8, each of the radiation patterns for the multiple antennas can be individually controlled by modifying the amplitude and/or phase. A wireless power reception apparatus such as, for example, wireless power reception apparatus 600 of FIG. 6 can, among other functions, dynamically control he cumulative antenna radiation pattern of an antenna array to radiate away from a user to reduce SAR, e.g., RF exposure to the user.

Figure 8:
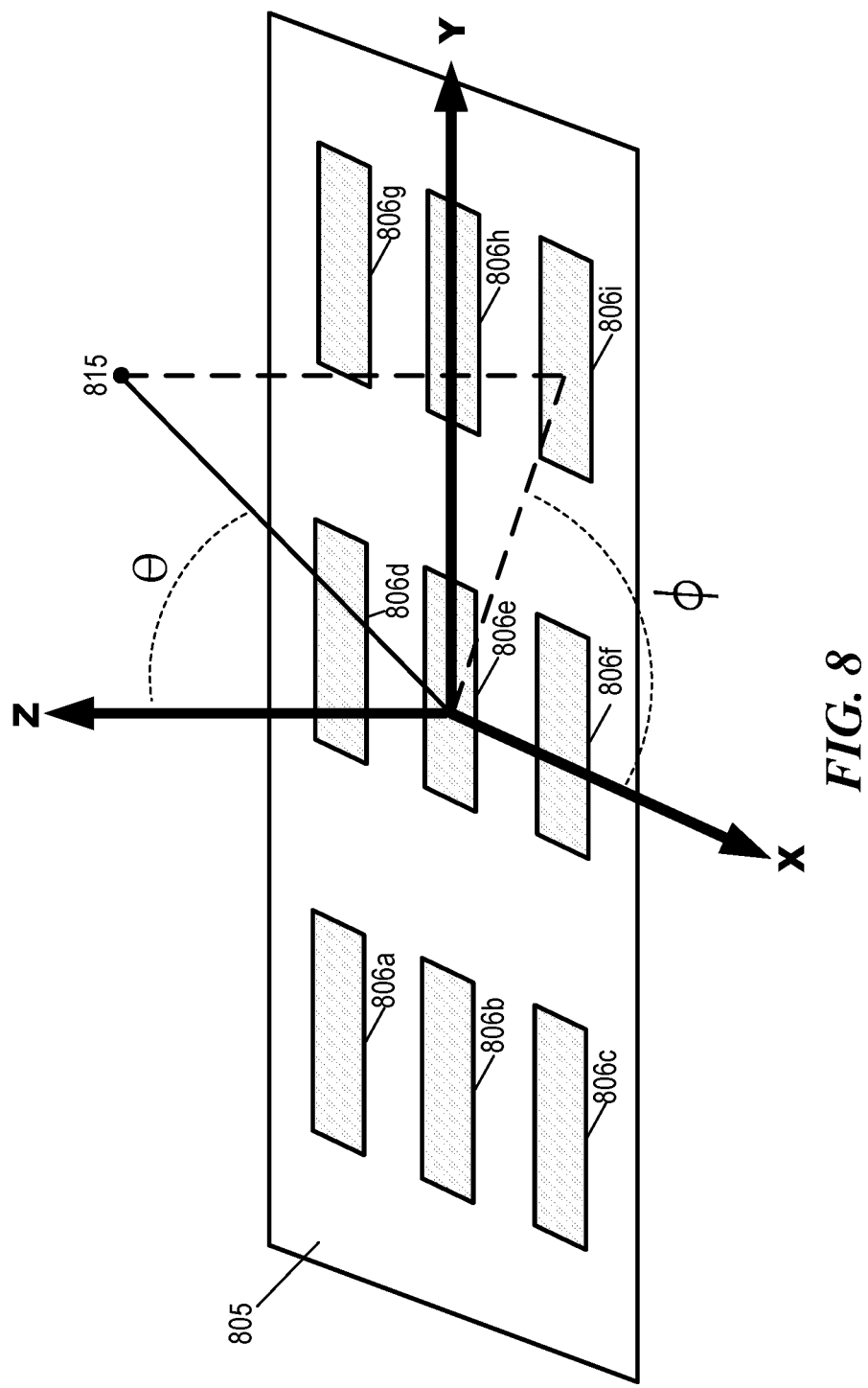
FIG. 8 illustrates an example of a more detailed antenna array 805 which includes nine antennas 806a-i each having a corresponding antenna radiation pattern that can be controlled over amplitude and phase.

FIG. 8 illustrates an example of a more detailed antenna array 805 which includes nine antennas 806a-i each having a corresponding antenna radiation pattern that can be controlled over amplitude and phase. More specifically, the directionality and/or a type of radiation pattern can be adjusted by modifying the amplitude and/or phase of the corresponding radiation pattern. As discussed herein, a wireless power reception apparatus can adjust the amplitude and/or phase of each antenna to direct the cumulative radiation pattern away from a user of a device in which the antenna array 805 is embedded. The antenna array 805 can be antenna array 705 of FIG. 7, although alternative configurations are possible. Antenna array 805 is shown with nine antennas shown for purposes of illustration only. It is appreciated that antenna array 805 can include any number of antennas.

As shown in equation 1, the total (or cumulative) radiation pattern $E_T$ is the vector summation of the radiation patterns of each individual antenna $E_i(\theta, \phi)$:

$$E_T(\theta,\phi)=\Sigma_{i=1}^{n} E_i(\theta,\phi) \times A_i \times e^{j\psi_i}, \quad \text{[Equation 1]}$$

where $A_i$ represents the amplitude of antenna i and $\psi_i$ represents the phase of antenna i.

In some embodiments, the wireless power reception apparatus is configured such that the maximum radiation is directed away (outwards) from the user of the wireless device. For example, the wireless power reception apparatus can be configured to adapt and/or otherwise modify the radiation pattern such that it accepts more power when the antenna array 805 is further from the head or body of the user or is oriented in a manner such that the antenna array 805 receives most power in a direction opposite the user and little or no power in other directions.

Figure 9:
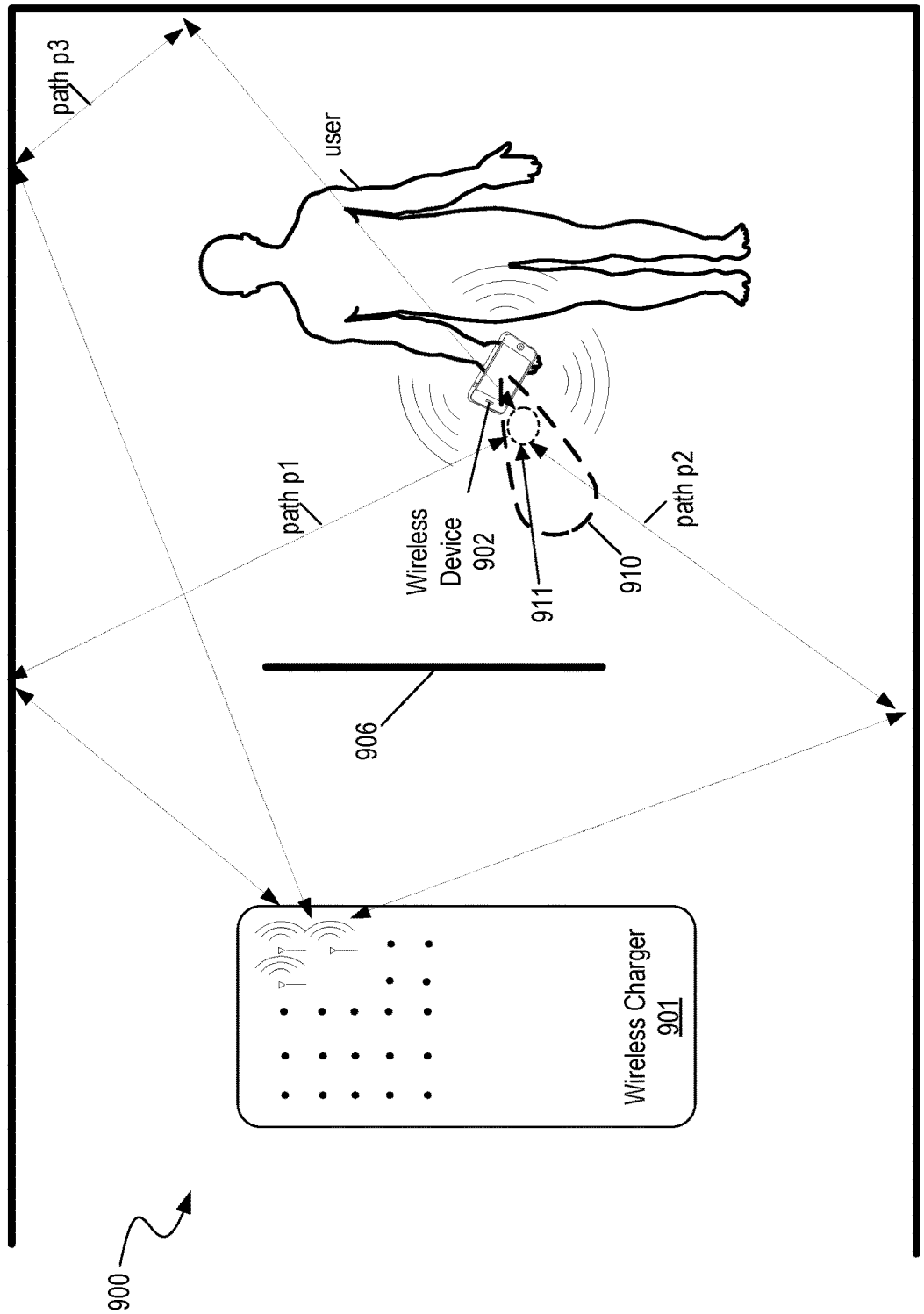
FIG. 9 depicts a diagram illustrating an example multipath wireless power delivery environment 900, according to some embodiments.

FIG. 9 depicts a diagram illustrating an example multi-path wireless power delivery environment 900, according to some embodiments. The multi-path wireless power delivery environment 900 includes a user operating a wireless device 902 including a wireless power reception apparatus such as, for example, wireless power reception apparatus 600 of FIG. 6. The charger 901 and the wireless device 902 can be charger 101 and wireless device 102 of FIG. 1, respectively, although alternative configurations are possible.

As shown in the example of FIG. 9, the multi-path wireless power delivery environment 900 includes reflective objects 106 and various absorptive objects, e.g., users or humans, etc. In operation, the wireless device 902 broadcasts a beacon signal that is received at the charger 901 via paths p1-p3. The charger subsequently transmits wireless power via paths p1-p3 to the wireless device 902. Three paths are shown in the example of FIG. 9 for simplicity, it is appreciated that any number of paths can be utilized.

As discussed herein, the wireless power reception apparatus of wireless device 902 can be configured to adapt and/or otherwise dynamically modify the radiation pattern 910 such that it accepts more power when the antenna array (not shown) is further from the head or body of the user or oriented in a manner such that the antenna array receives most power in a direction opposite the user and receives little or no power in other directions.

Figure 10:
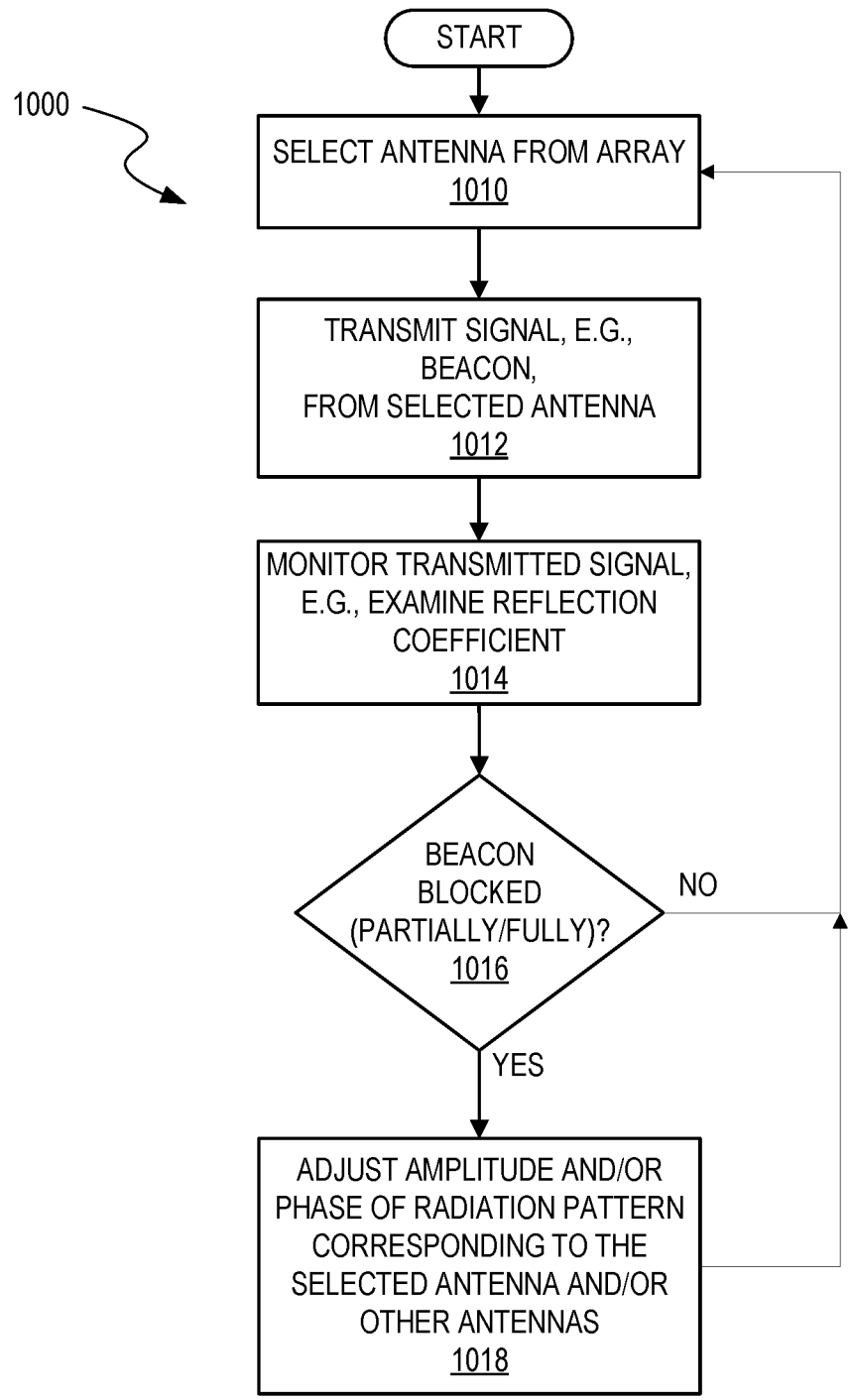
FIG. 10 depicts a flow diagram illustrating an example process for dynamically adjusting radiation transmission and reception patterns based on monitored transmitted signals, e.g., beacon signals.
Figure 11:
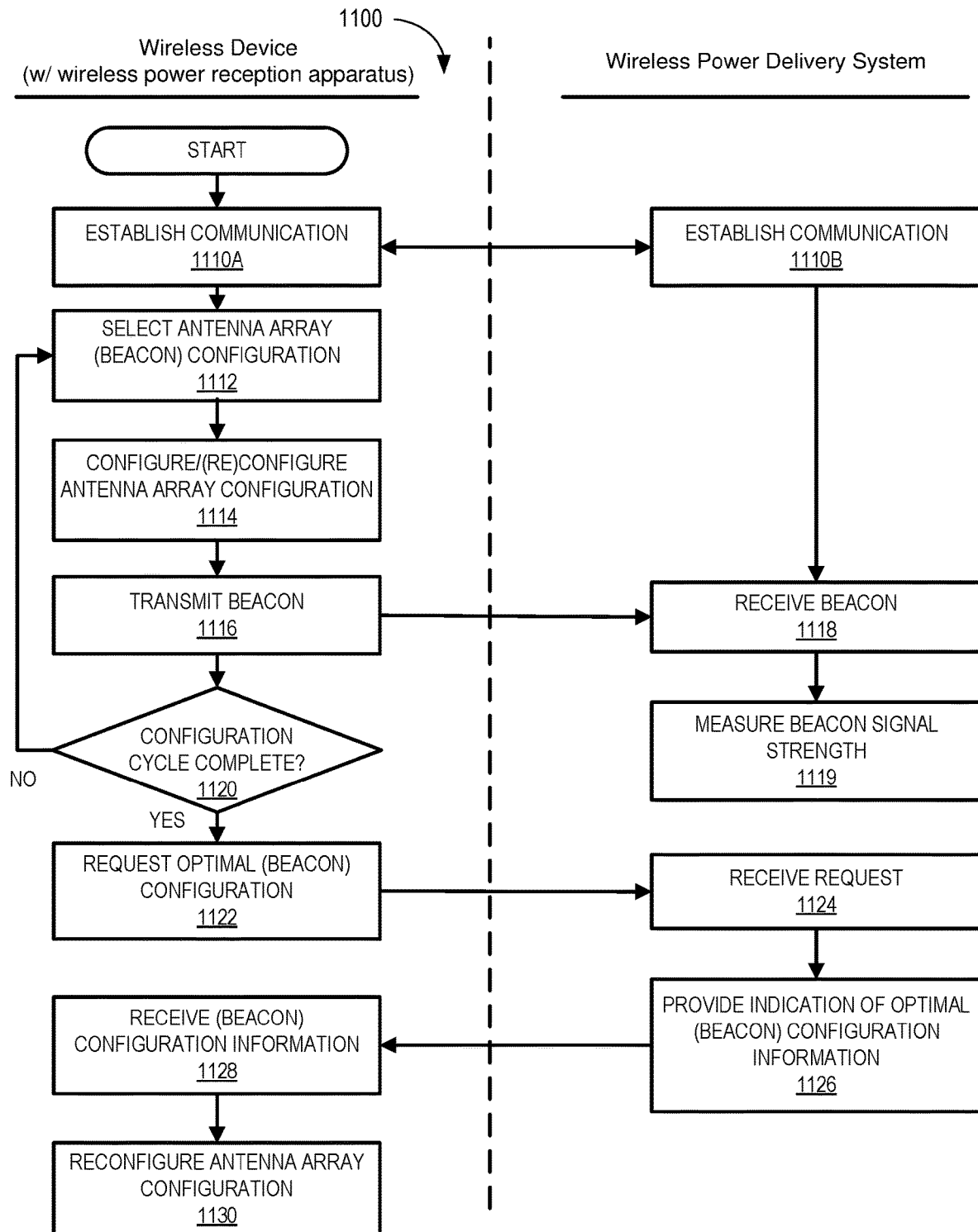
FIG. 11 depicts a flow diagram illustrating an example process 1000 for dynamically reconfiguring antenna array configurations, according to some embodiments.

Furthermore, the precise location of the RF energy pocket 911 (or power ball) and/or the angle of incidence of the RF energy received at the RF energy pocket 911 (or power ball) can be controlled via modification to the radiation pattern 910 to reduce and/or otherwise avoid absorption of wireless energy, e.g., RF energy, by human flesh of user that is proximate to the wireless device 902. As discussed herein, the modifications to the radiation pattern 910 can be made via amplitude and/or phase adjustments to one or more antennas of an antenna array of the wireless device 902. FIGS. 10 and 11 discusses example techniques for dynamically modifying radiation patterns, according to various embodiments. Other techniques are also possible.

FIG. 10 depicts a flow diagram illustrating an example process 1000 for dynamically adjusting transmission and reception radiation patterns based on monitored transmitted signals, e.g., beacon signals. More specifically, the example process 1000 illustrates a process for detecting potential blockage or obstructions, e.g., user holding the electronic device is such a way as to cause one or more antennas to be fully or partially blocks. An electronic device having an embedded wireless power reception apparatus, e.g., control system or control logic of a wireless power reception apparatus control system can, among other functions, perform the corresponding steps of example process 1000. The wireless power reception apparatus can be wireless power reception apparatus 600 of FIG. 6, although alternative configurations are possible. Process 1000 can be a continuous process, can be commenced responsive to movement of the device, periodically, etc., including combinations and/or variations thereof.

To begin, at process 1010, the electronic device selects a first antenna from an antenna array, e.g., antenna array 630 of FIG. 6. At process 1012, the electronic device transmits a beacon signal from the selected antenna. At step 1014, the electronic device monitors and/or otherwise listens for the transmitted signal or reflections thereof, e.g., with the remaining antennas and/or with the transmitting antenna. At decision process 1016, the electronic device determines if an obstruction is partially or fully blocking the beacon signal. For example, in some embodiments, the electronic device can capture and process the reflection coefficient of the antenna to determine if any power is reflected. If power is reflected, the then the electronic device can conclude that an obstruction exists. In some embodiments, the reflected power or reflection coefficient must exceed a threshold for the electronic device to conclude that an obstruction exists. Moreover, in some embodiments, the reflected power and/or other environmental factors can be utilized to determine the type of obstruction.

If an obstruction exists, at step 1018, the electronic device adjusts the amplitude and/or phase corresponding to the selected antenna and/or other antennas. For example, if an obstruction exists, the electronic device may determine that the obstruction is likely a human holding the device and decrease the amplitude corresponding to that antenna to reduce SAR, e.g., RF exposure to the user. In some embodiments, the amplitude and phases of the other antennas of the array might also be adjusted to direct the cumulative transmission and reception radiation pattern of the antenna away from the user.

FIG. 11 depicts a flow diagram illustrating an example process 1100 for cycling through the preconfigured radiation patterns, e.g., antenna array (beacon) configurations, to dynamically identify a configuration or radiation pattern that results in lowest SAR, e.g., RF exposure to the user, according to some embodiments. A wireless device having an embedded wireless power reception apparatus, e.g., control system or control logic of a wireless power reception apparatus control system can, among other functions, perform the corresponding steps of example process 1100. The wireless power reception apparatus can be wireless power reception apparatus 600 of FIG. 6, although alternative configurations are possible. The wireless power delivery system can be a wireless charger or components of a wireless charger, e.g., a wireless charger 101 of FIG. 1 or wireless charger 300 of FIG. 3, and/or a processing system, e.g., control logic 310 of FIG. 3. Alternative configurations are also possible.

In some embodiments, the wireless power reception apparatus, e.g., control system or control logic of a wireless power reception apparatus control system will have various preconfigured radiation patterns that can be cycled through or selected to select an optimal antenna (beacon) configuration. In some embodiments, the optimal antenna (beacon) configuration is the configuration in which the wireless power delivery system receives beacons having the strongest signal strength. In some embodiments, this configuration indicates the fewest obstructions and thus provides a configuration that results in lowest SAR, e.g., RF exposure to the user. It is appreciated that other methodologies for cycling through antenna (beacon) configurations to identify the configuration that results in lowest SAR are also possible.

To begin, at processes 1110A and 1110B, communication is established between the wireless device and the wireless power delivery system. Once communication is established between the wireless device and the wireless power delivery system, at process 1112, the wireless device selects an antenna array configuration, e.g., a configuration for transmission and reception using a particular cumulative radiation pattern. As discussed herein, in some embodiments, the configuration can indicate particular amplitudes and phases for each antenna in the array. At process 1114, the wireless device configures the antenna array based on the selected configuration and, at process 116 transmits a beacon signal based on the antenna configuration. At process 118, the wireless power delivery system receives the beacon and, at process 1119, measures the beacon signal strength. The wireless device might send one or multiple beacons using the selected configuration, however, in this example, a signal beacon is transmitted.

At decision process 1120, the wireless device determines if the configuration cycle is complete. As discussed herein, there can be any number of predetermined configurations. If the cycle is not complete, then a new configuration is selected at process 112 and the process continues as discussed above. If the cycle is complete, then at process 1122, the wireless device requests the configuration information, e.g., the optimal configuration as determined by the wireless power delivery system. At process 1124, the wireless power delivery system receives the request and, at process 1126, provides the wireless device with the requested configuration information. At process 1128, the wireless device receives the configuration information and lastly, at process 1130, configures the antenna array with the optimal array configuration.

B. Glass Front Antenna(s)

FIGS. 12A-12F depict various diagrams illustrating additional techniques for reducing human exposure to wireless energy, e.g., RF energy, in wireless power delivery environments utilizing glass front antennas. The various components discussed with reference to FIGS. 12A-12F may be the components discussed with reference to FIG. 1. For example, device 1202 and charger 1201 can be wireless device 102 and charger 101 of FIG. 1, respectively. Alternative configurations are also possible.

Figure 12A:
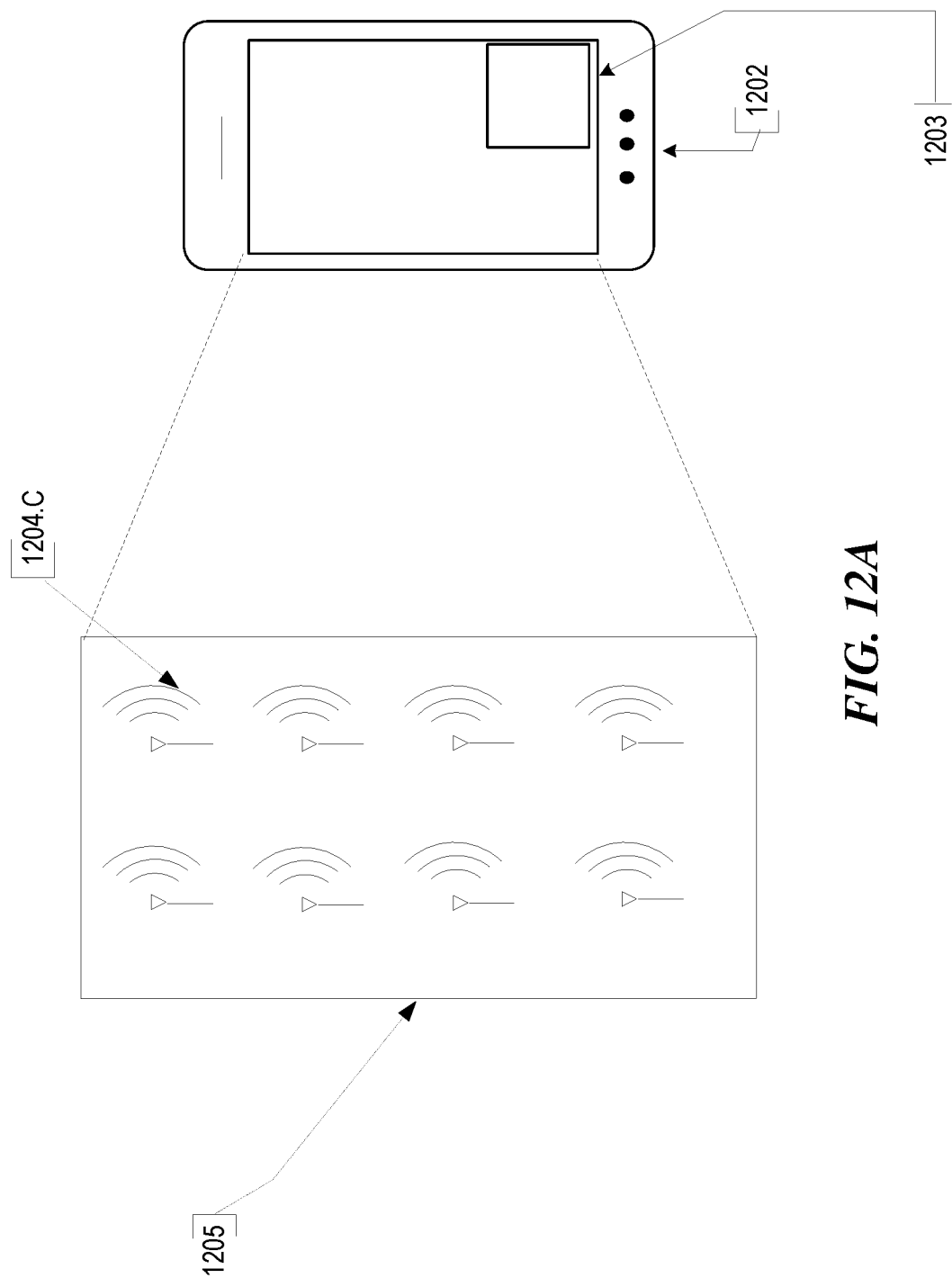
FIGS. 12A-12F depict various diagrams illustrating additional techniques for reducing human exposure to wireless energy, e.g., RF energy, in wireless power delivery environments utilizing glass front antennas.

Referring first to FIG. 12A, which depicts a diagram illustrating example device having multiple glass screen antennas 1204.c, according to some embodiments. As discussed herein, in some embodiments, the antennas work in conjunction to phase the beacon in a parallel polarization to avoid sending the beacon towards (in the direction of) the device holder. In some embodiments, a software-based antenna lobe pattern management scheme is utilized which directs the wireless power/data back to the same antennas in the same fashion the beacon was sent. Signals emitted by the glass based antenna array do not have to be beam forming or directional, but instead can be tailored for multipath environments.

Figure 12B:
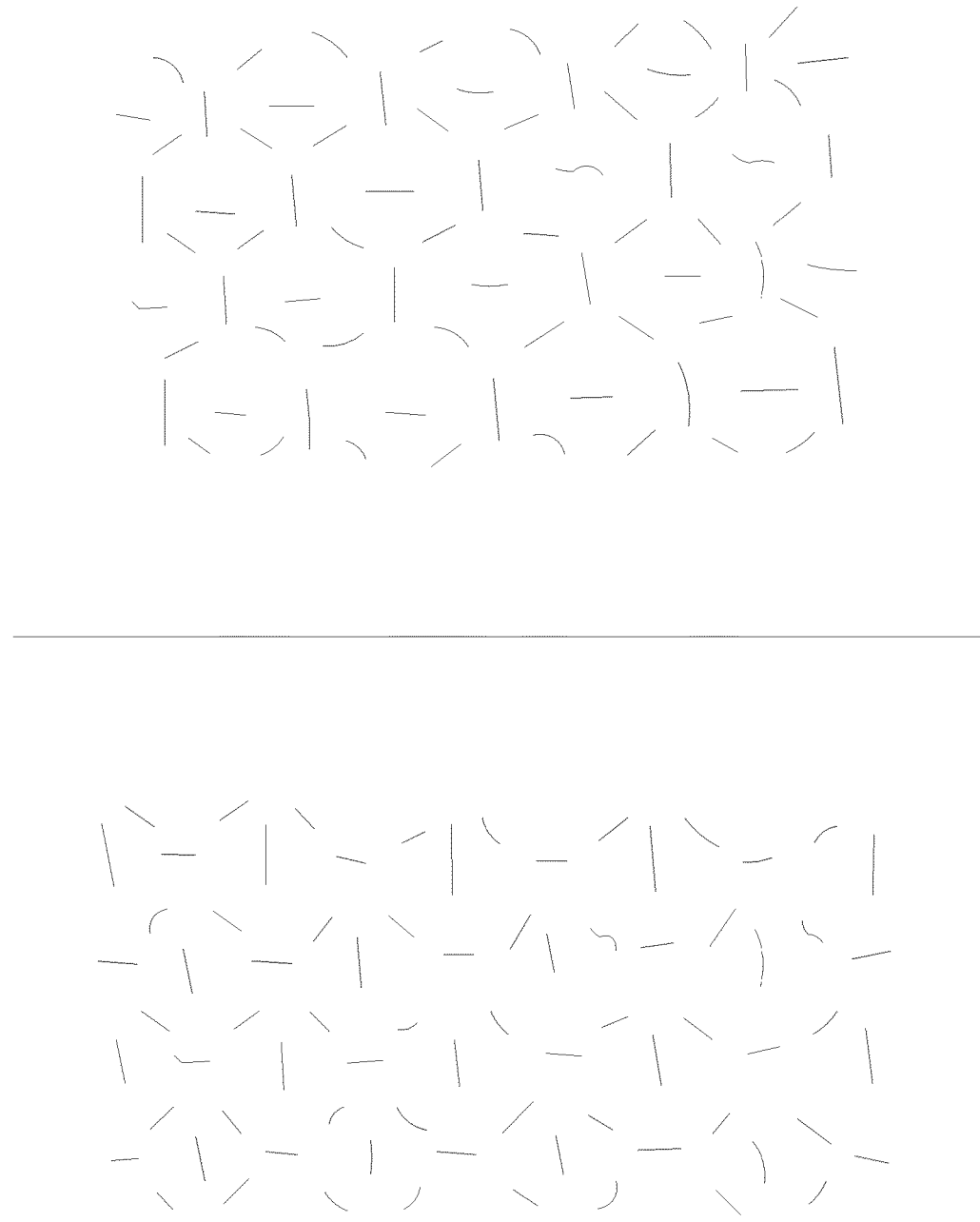

FIG. 12B depicts a diagram illustrating an example arrangement of antennas 1204.c, according to some embodiments. More specifically, FIG. 12B illustrates an efficient quasicrystal antenna layout, according to some embodiments. Other efficient arrangement of the antennas can be used to enhance the beacon broadcasting and the power/data delivery to the device 1202. In some embodiments, the antennas 1204.c can be fractal self-similarity antennas or have various arrangements to provide enhanced communication such as quasicrystal or otherwise.

Figure 12C:
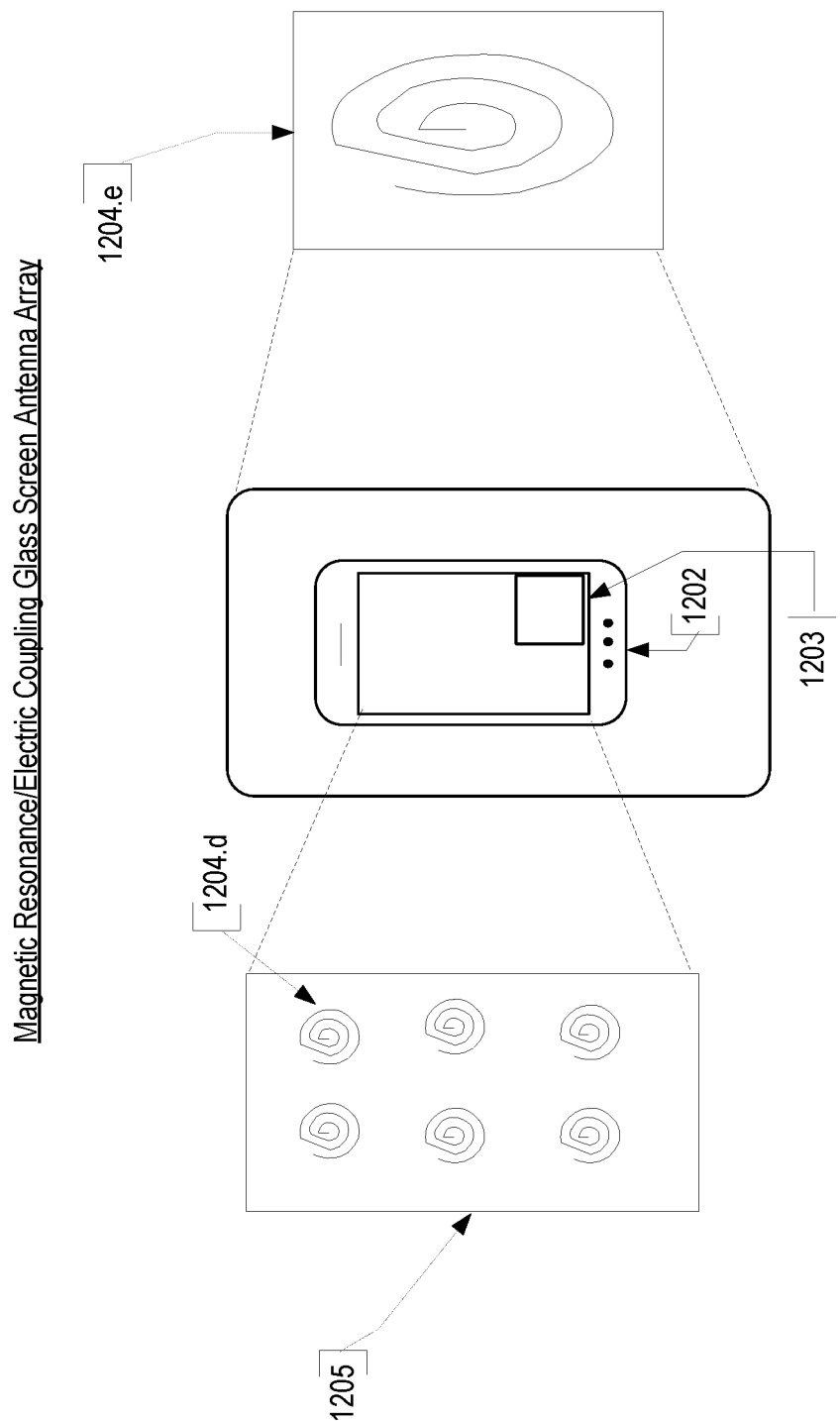

The techniques described herein are applicable with other forms or wireless power/data delivery such as magnetic resonance or electric coupling. For example, the antennas 1204.c can be coils that work in conjunction with another surface as a charging coil ring as shown in FIG. 12C. Utilizing small, transparent or opaque coils or antenna placed above or below a display or glass cover over intended device/system, these antennae can be utilized to receive magnetic, electric field or RF wireless power that can be harvested for use by the local electronics, battery or device.

Figure 12D:
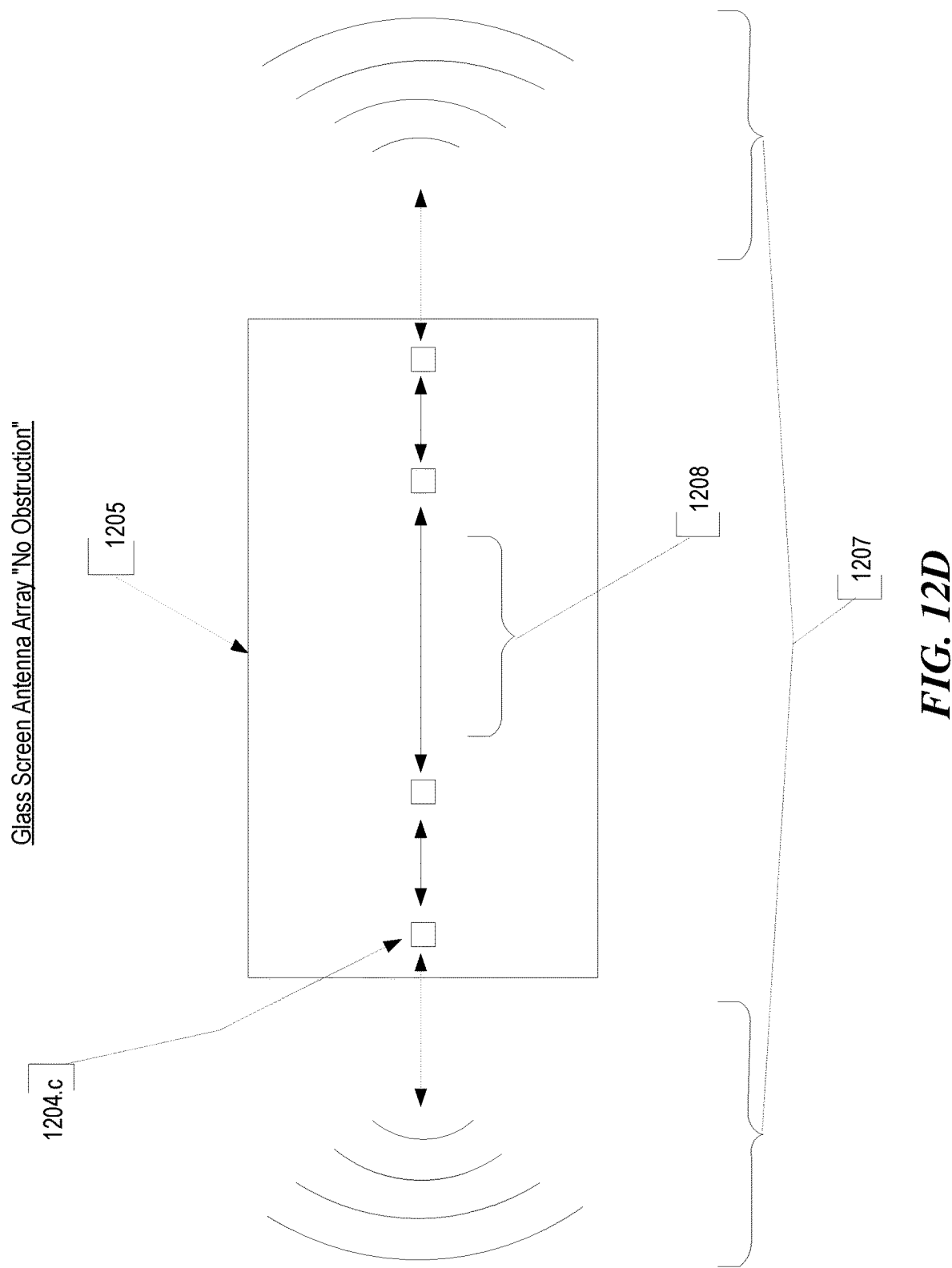

FIG. 12D depicts a diagram illustrating an initial beacon broadcasting while no obstruction is present, according to some embodiments. Various algorithms such as, for example, genetic algorithm or annealing algorithm can be applied to find the optimum phase for the beacon 1207. This technique can reduce or eliminate the absorbed beacon 1207 by the human body 1210. More importantly, this technique provides more powerful and targeted beacon to the charger 1201 which leads to stronger and isolated power/data delivery to the wireless device 1202 comprising the antennas 1204.c. As discussed above, the isolated power delivery to the wireless device is also referred to herein as an RF energy pocket or power ball because the wireless energy is focused by the charger over the multiple paths in which the beacon signal is received to the precise location from which the beacon is transmitted.

Figure 12E:
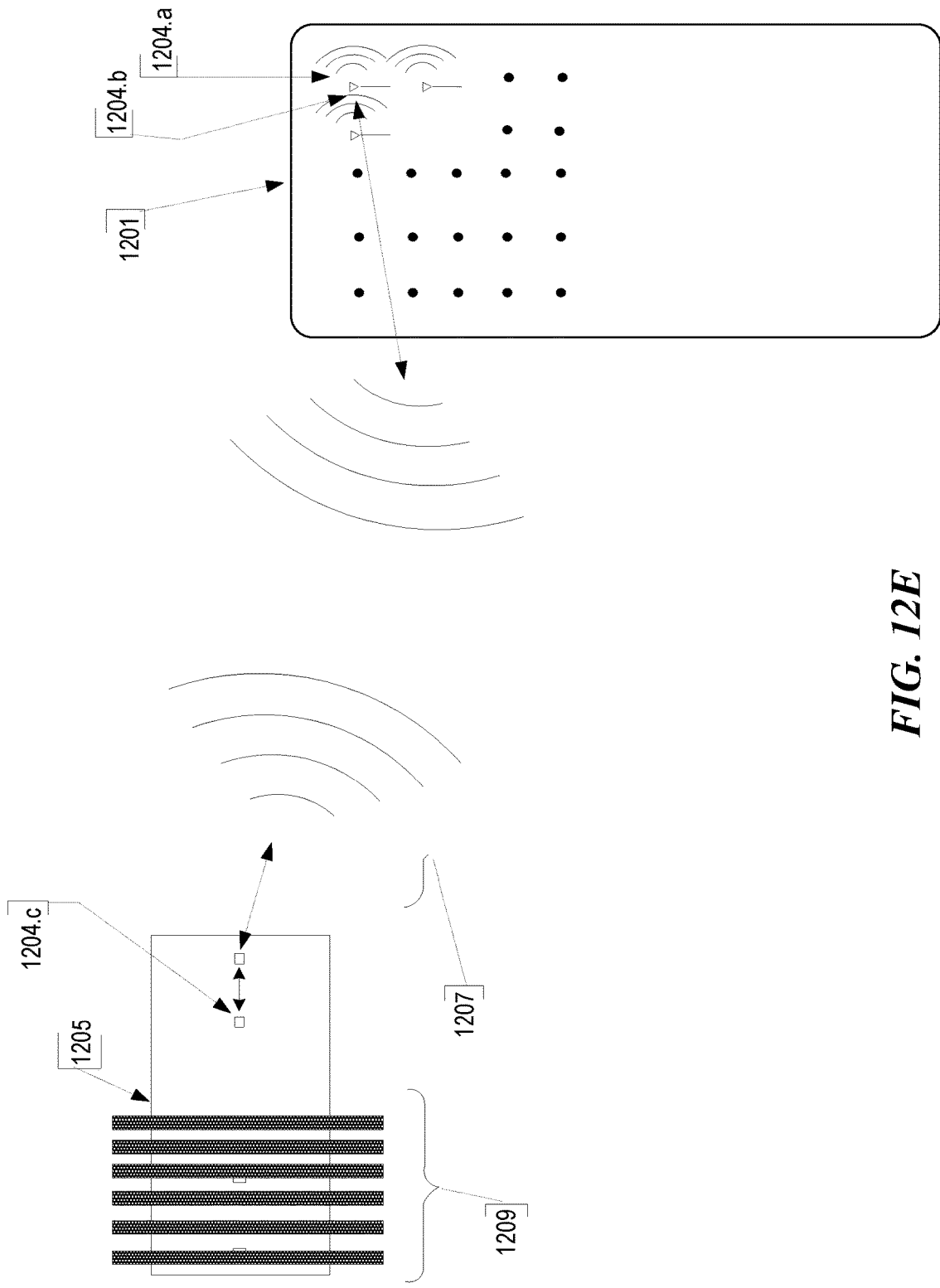

FIG. 12E depicts a diagram illustrating an embodiment whereby at least some of the antennas 1204.c are blocked by an object 1209. With antennas on one or both sides of a device, the beacon will be emitted from all the antennas, but for blocked antennas, their beacon will not travel as efficiently as the open/free antennas, and the power will be returned to the open/free antenna and not to the obscured antennas. This is also true for any other algorithm that can determine the efficiency of power delivery to each antennae and allow the transmitter to focus its signal on the open/free antennas.

Figure 12F:
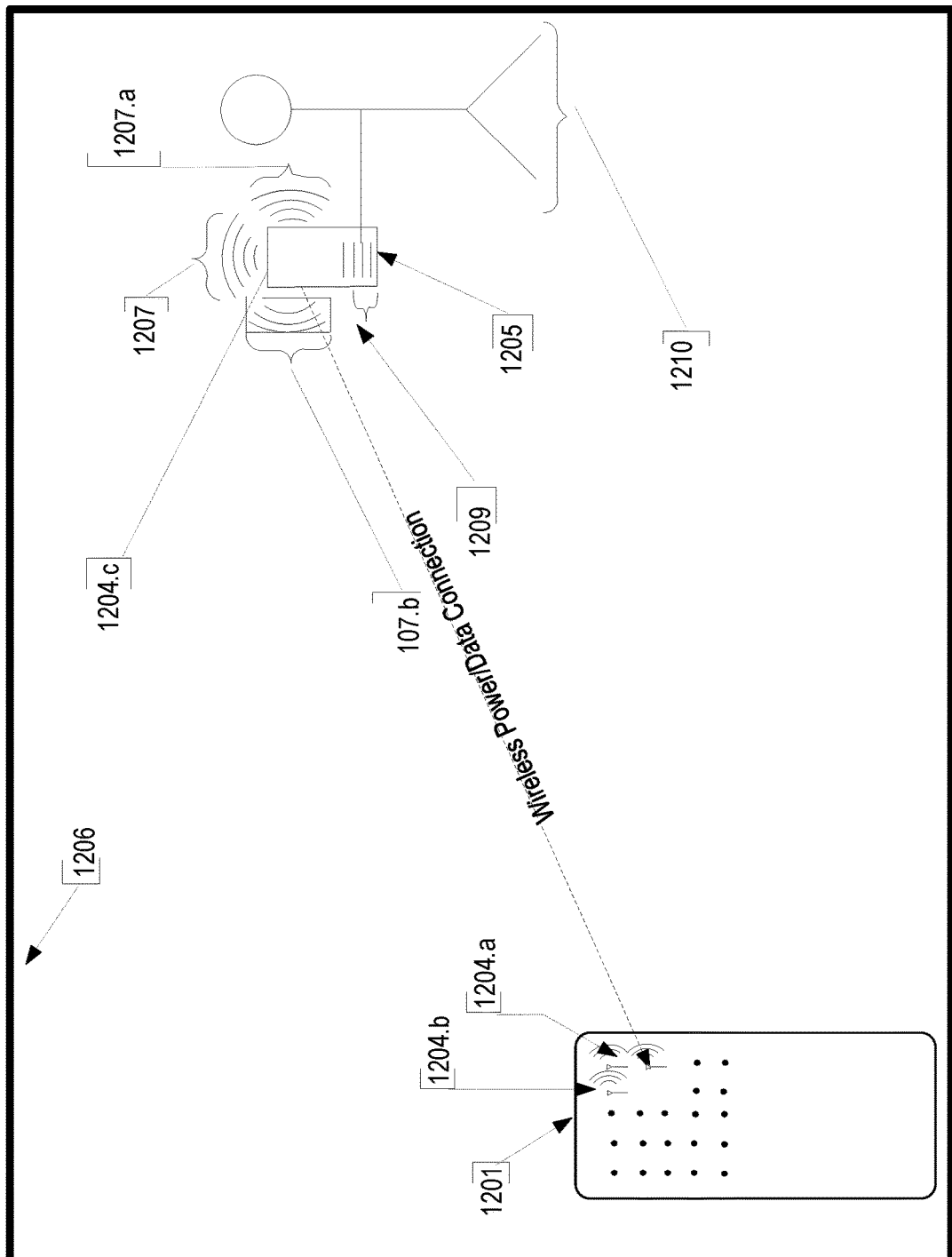

FIG. 12F depicts a diagram illustrating a general embodiment of the system whereby a human body (or human flesh) 1210 is present in an environment where a charger 1201 and a wireless device 1202 are present. More specifically, the example of FIG. 12F illustrates the beacon broadcasting and the power delivery in the presence of a user 1210. The client 1203 utilizes the wireless device surface 1205 to broadcast the beacon from the external antennas 1204.c. The beacon 1207 initially broadcasts in several directions as shown in FIG. 8. The beacon power is almost negligible compared to the delivered power/data signal to the device 1202. The charger 1201 only corresponds to the beacon signal 1207.b that lands in the charger 1201 direction. The beacon signal 1207.a will not result in power/data signal delivery by the charger 1201 because it's not directed towards the charger 1201. The antennas 1204.c will utilize a beacon broadcasting algorithm to phase the broadcasted beacon towards 1201. This technique avoids undesired directivity of the beacon signal such as 1207.a. In addition to this, this technique will result in a stronger phased beacon towards the charger 1201 which leads to a stronger and more efficient power/data signal delivery without exposing the flesh of the user 1210 to RF power.

Several factors can affect SAR levels; one of these factors is the angle of incidence of the received RF signal on the human skin. Human skin can exhibit different RF absorption levels depending on the incidence angle. Vertical (horizontal) polarized angles of incidence lead to more absorption and less reflection by a dielectric material "human skin". On the other hand, parallel-polarized angles of incidence lead to more reflection and less absorption by a dielectric material "human skin" which is more desirable.

In some embodiments, the techniques described herein control the polarization of the glass screen antennas and/or the angles of incidence to reduce and avoid absorption by the human skin. This leads to a stronger broadcasted beacon signal which leads to more delivered power/data to the wireless device 1202. The controlled polarization of the glass screen antennas minimizes the absorbed power onto the human flesh, which is highly desired. If this technique isn't utilized, human flesh 1210 can be exposed to undesired RF signal which leads to high absorption level rates which consequently will lead to low beacon and power reception to the wireless device 1202.

As discussed herein, one technique that can be utilized to reduce SAR levels is to increase the aperture, e.g., number of antennas 1204.*c* on the wireless device 1202 as shown in FIGS. 12A and 12B. This technique allows the received power signal to be distributed over the surface of the wireless device 1202, rather than on a specific area or individual antenna on the device.

In some embodiments, the antennas 1204.*c* can be oriented in different forms to optimize the beacon received by the charger 1201 and to maximize the power received by the device 1202. For example, the glass front antennas can be arranged in a quasi-crystal format as shown in the example of FIG. 12B. Alternatively or additionally, in some embodiments, the glass front antennas can be placed in a self-similarity "fractal" orientation to optimize signal transmission.

Moreover, as discussed, the antennas 1204.*c* can phase transmitted beacon signals to broadcast an optimum beacon. By way of example and not limitation, in some embodiments, an annealing algorithm or genetic algorithm can be used to calculate the best phase for the beacon broadcasting. This technique provides a filtered and more efficient path for the beacon, since a beacon exiting several antennas will naturally have directivity—whether on purpose or not. As discussed, the charger can utilize the same path for wireless power/data delivery as the received beacon. This technique avoids absorption of the RF signal by the human flesh by creating RF energy pockets or power balls.

The charger is configured such that if there is no beacon received from the client; there will be no power delivery. This technique avoids delivering power to undesired locations.

In case of obstruction of some of the glass screen antennas 1204.*c* by a material that may be but not limited to 1209. The non-obstructed antennas can carry the weight of the obstructed antennas. The non-obstructed antennas will broadcast the beacon and receive the allocated wireless power/data from the charger. This technique avoids delivering power to the obstructed areas of the device avoiding the absorption of RF power signal by human flesh as shown in FIG. 12F.

Embodiments of the present disclosure describe techniques for reducing SAR levels and utilizing the screen of the wireless devices as an antenna array for broadcasting a phased beacon which leads to a more filtered and focused wireless power/data delivery. The techniques are performed in various ways as disclosed. Furthermore, as disclosed herein, the techniques can be performed at a charger system and/or a wireless device. These techniques can be used for a variety of functions. By way of example and not limitation, the techniques described herein can be used in various industrial, military and medical applications, etc.

It is appreciated that various techniques discussed herein reduce the special absorption rate (SAR) levels at the receiving end of the RF power signal. In some embodiments, techniques can utilize a glass screen of the wireless device as an antenna array in different orientations. These techniques achieve at least, but not limited to, the following: delivering wireless power while maintaining exposure limits, avoiding exposing flesh to undesired RF signal levels, maintaining wireless power delivery efficiency, enabling devices to receive wireless power and data regardless of the positioning of the device, allowing a device screen to broadcast beaconing signals, and allowing the device screen to receive the power signal from any direction without exceeding the FCC "SAR" limitations (1.6 mW/cm$^3$).

In some embodiments, the antennas 1204.*c* can be placed anywhere on or within the wireless powered electronic device. The antennas 1204.*c* can be in the form of an additional screen that can be placed on the wireless device 1202 to provide the same functionality as if its built in the wireless device 1202 screen. The system described herein can provide the same functionality for various types of signals other than RF power and data signals. The system described here in can work with various frequencies such as 5.8 GHz. Higher frequencies lead to higher flesh absorption because of the shorter wave length and the higher power levels it carries.

In some embodiments, the system described herein covers any form RF power signal delivery. The system described herein can be in different forms or sizes. By way of example and not limiting, the charger 1201 and the client 1203 can be in a form of an Application Specific Integrated Circuit "ASIC" chip. The antennas 1204.*c* can provide functionality without interfering with existing antennas and their functionality, e.g., WiFi and/or Bluetooth. The antennas 1204.*c* described in figures herein can utilize to receive magnetic, electric field or RF wireless power than be harvested for use by the local electronics, battery or device. In the examples discussed herein the embodiments can include a data communication module, which can be used to coordinate events.

Additionally, in some embodiments the beacon signal, which is primarily referred to herein as a continuous waveform, can alternatively or additionally take the form of a modulated signal. Furthermore, in some embodiments, wireless power delivery can be achieved between a charger 1201 and a wireless device 1202 without a broadcasted beacon signal.

III. Example Systems

Figure 13:
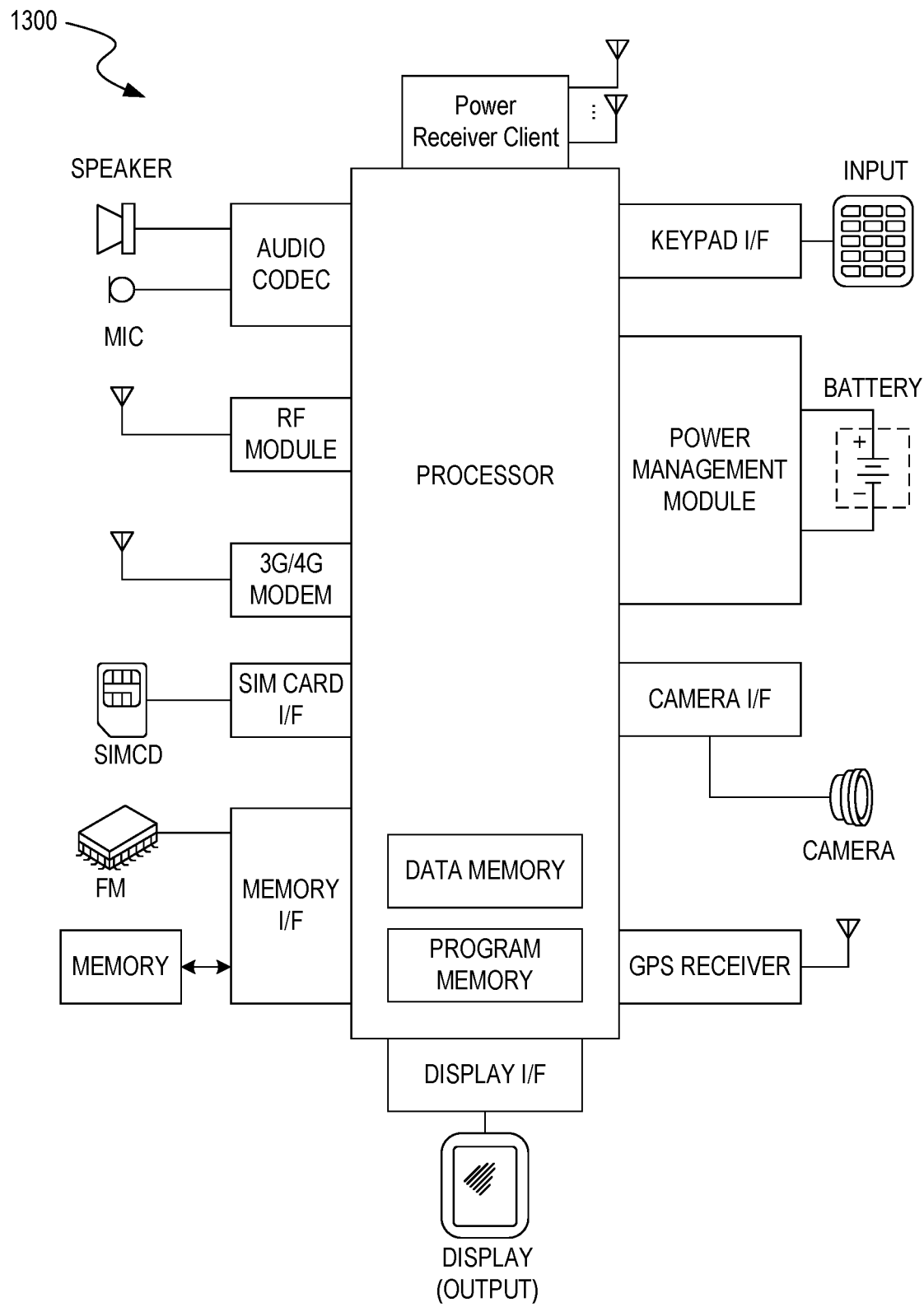
FIG. 13 depicts a block diagram illustrating example components of a representative mobile device or tablet computer with a wireless power receiver or client in the form of a mobile (or smart) phone or tablet computer device, according to some embodiments.

FIG. 13 depicts a block diagram illustrating example components of a representative mobile device or tablet computer 1300 with a wireless power receiver or client in the form of a mobile (or smart) phone or tablet computer device, according to an embodiment. Various interfaces and modules are shown with reference to FIG. 13, however, the mobile device or tablet computer does not require all of modules or functions for performing the functionality described herein. It is appreciated that, in many embodiments, various components are not included and/or necessary for operation of the category controller. For example, components such as GPS radios, cellular radios, and accelerometers may not be included in the controllers to reduce costs and/or complexity. Additionally, components such as ZigBee radios and RFID transceivers, along with antennas, can populate the Printed Circuit Board (PCB).

The wireless power receiver client can be a power receiver clients 103 of FIG. 1 or wireless power reception apparatus 600 of FIG. 6, although alternative configurations are possible. Additionally, the wireless power receiver client can include one or more RF antennas for reception of power and/or data signals from a charger, e.g., charger 101 of FIG. 1.

Figure 14:
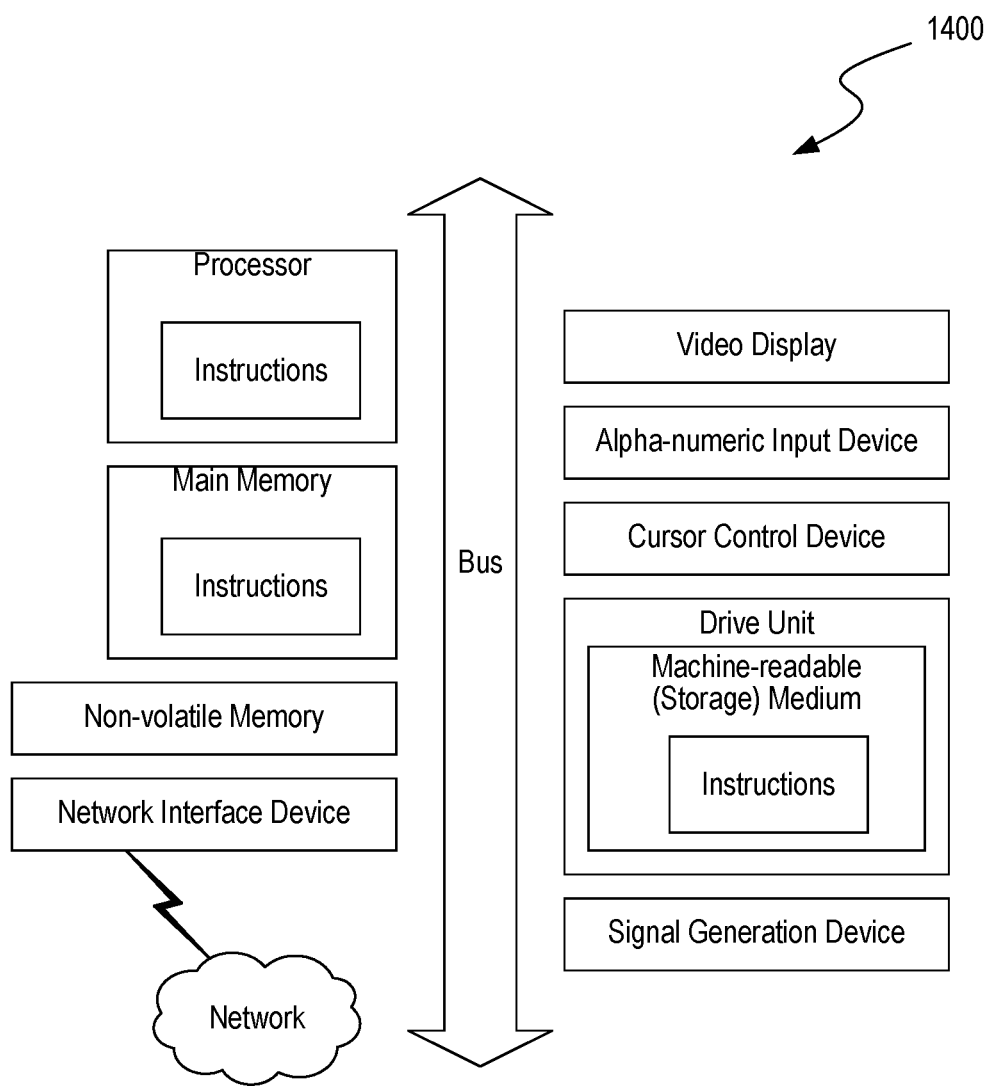
FIG. 14 depicts a diagrammatic representation of a machine, in the example form, of a computer system within which a set of instructions, for causing the machine to perform any one or more of the methodologies discussed herein, may be executed.

FIG. 14 depicts a diagrammatic representation of a machine, in the example form, of a computer system within which a set of instructions, for causing the machine to perform any one or more of the methodologies discussed herein, may be executed.

In the example of FIG. 14, the computer system includes a processor, memory, non-volatile memory, and an interface device. Various common components (e.g., cache memory) are omitted for illustrative simplicity. The computer system 1400 is intended to illustrate a hardware device on which any of the components depicted in the example of FIGS. 1-12 (and any other components described in this specification) can be implemented. For example, the computer system can be any radiating object or antenna array system. The computer system can be of any applicable known or convenient type. The components of the computer system can be coupled together via a bus or through some other known or convenient device.

The processor may be, for example, a conventional microprocessor such as an Intel Pentium microprocessor or Motorola power PC microprocessor. One of skill in the relevant art will recognize that the terms "machine-readable (storage) medium" or "computer-readable (storage) medium" include any type of device that is accessible by the processor.

The memory is coupled to the processor by, for example, a bus. The memory can include, by way of example but not limitation, random access memory (RAM), such as dynamic RAM (DRAM) and static RAM (SRAM). The memory can be local, remote, or distributed.

The bus also couples the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer 900. The non-volatile storage can be local, remote, or distributed. The non-volatile memory is optional because systems can be created with all applicable data available in memory. A typical computer system will usually include at least a processor, memory, and a device (e.g., a bus) coupling the memory to the processor.

Software is typically stored in the non-volatile memory and/or the drive unit. Indeed, for large programs, it may not even be possible to store the entire program in the memory. Nevertheless, it should be understood that for software to run, if necessary, it is moved to a computer readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium". A processor is considered to be "configured to execute a program" when at least one value associated with the program is stored in a register readable by the processor.

The bus also couples the processor to the network interface device. The interface can include one or more of a modem or network interface. It will be appreciated that a modem or network interface can be considered to be part of the computer system. The interface can include an analog modem, isdn modem, cable modem, token ring interface, satellite transmission interface (e.g. "direct PC"), or other interfaces for coupling a computer system to other computer systems. The interface can include one or more input and/or output devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the example of FIG. 9 reside in the interface.

In operation, the computer system 1400 can be controlled by operating system software that includes a file management system, such as a disk operating system. One example of operating system software with associated file management system software is the family of operating systems known as Windows® from Microsoft Corporation of Redmond, Wash., and their associated file management systems. Another example of operating system software with its associated file management system software is the Linux operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are, at times, shown as being performed in a series, these processes or blocks may instead be performed in parallel, or may be performed at different times. Further, any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference. Aspects of the disclosure can be modified, if necessary, to employ the systems, functions, and concepts of the various references described above to provide yet further embodiments of the disclosure.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will begin with the words "means for".) Accordingly, the applicant reserves the right to add additional claims after filing the application to pursue such additional claim forms for other aspects of the disclosure.

The detailed description provided herein may be applied to other systems, not necessarily only the system described above. The elements and acts of the various examples described above can be combined to provide further implementations of the invention. Some alternative implementations of the invention may include not only additional elements to those implementations noted above, but also may include fewer elements. These and other changes can be made to the invention in light of the above Detailed Description. While the above description defines certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention.

What is claimed is:

1. An apparatus comprising:
   means for receiving wireless power from a wireless power transmission system in a wireless power delivery environment;
   means for providing the received wireless power to an electronic device or an energy storage apparatus adapted to power the electronic device; and
   means for reducing wireless energy exposure to a user of the electronic device by directing one or more of multiple wireless communication means disposed on or within the electronic device to dynamically adjust a cumulative radiation pattern.

2. The apparatus of claim 1, further comprising:
   the multiple wireless communication means,
   wherein each of the multiple wireless communication means has a corresponding radiation patterns that is adjustable over one or more of amplitude and phase, and
   wherein the radiation patterns collectively comprise the cumulative radiation pattern.

3. The apparatus of claim 1, further comprising:
   means for detecting one or more full or partial blockages of radiation patterns corresponding to the multiple wireless communication means.

4. The apparatus of claim 3, wherein the cumulative radiation pattern is adjusted based on the one or more full or partial blockages of the radiation patterns corresponding to the multiple wireless communication means.

5. The apparatus of claim 1, further comprising:
   means for detecting an orientation of the cumulative radiation pattern relative to the user of the electronic device.

6. The apparatus of claim 5, wherein the cumulative radiation pattern is adjusted based, at least in part, on the orientation of the cumulative radiation pattern relative to the user of the electronic device.

7. The apparatus of claim 1, wherein to dynamically adjust the cumulative radiation pattern, the means for reducing wireless energy exposure adjust a direction or intensity of a beacon signal transmitted by the multiple communication means.

8. The apparatus of claim 1, wherein to dynamically adjust the cumulative radiation pattern, the means for reducing wireless energy exposure adjust an angle of incidence of the wireless power received from the wireless power transmission system.

9. The apparatus of claim 1, wherein to dynamically adjust the cumulative radiation pattern, the means for reducing wireless energy exposure cycle through a set of fixed cumulative radiation patterns to identify a configuration that results in the lowest amount of wireless energy exposure to the user of the electronic device.

10. The apparatus of claim 1, wherein to dynamically adjust the cumulative radiation pattern, the means for reducing wireless energy exposure adjust the cumulative radiation pattern in a direction away from the user of the electronic device.

11. A wireless power reception apparatus comprising:
    a control system configured to direct antennas of an electronic device to dynamically adjust a cumulative radiation pattern to reduce wireless energy exposure to a user of the electronic device,
    wherein the wireless power reception apparatus is configured to wirelessly receive power from a wireless power delivery system in a wireless power delivery environment.

12. The wireless power reception apparatus of claim 11, further comprising:
    the multiple antennas,
    wherein the multiple antennas have corresponding radiation patterns that are adjustable over one or more of amplitude and phase by the control system,
    the radiation patterns collectively comprising the cumulative radiation pattern.

13. The wireless power reception apparatus of claim 12, wherein the control system is further configured:
    detect one or more full or partial blockages of the radiation patterns corresponding to the multiple antennas,
    wherein the cumulative radiation pattern is adjusted based, at least in part, on the one or more full or partial blockages.

14. The wireless power reception apparatus of claim 11, wherein the control system is further configured to:
  detect an orientation of the cumulative radiation pattern relative to the user of the electronic device, and
  wherein the cumulative radiation pattern is adjusted based on the orientation of the cumulative radiation pattern relative to the user of the electronic device.

15. The wireless power reception apparatus of claim 11, wherein the control system is further configured to:
  adjust a direction or intensity of a beacon signal transmitted by one or more of the multiple antennas.

16. The wireless power reception apparatus of claim 11, wherein to dynamically adjust the cumulative radiation pattern, the control system is configured to:
  adjust an angle of incidence of the wireless power received from the wireless power delivery system.

17. The wireless power reception apparatus of claim 11, wherein to dynamically adjust the cumulative radiation pattern, the control system is configured to:
  cycle through a set of fixed cumulative radiation patterns to identify an antenna configuration that results in the lowest wireless energy exposure to the user of the electronic device.

18. The wireless power reception apparatus of claim 11, wherein to dynamically adjust the cumulative radiation pattern, the control system is configured to:
  adjust the cumulative radiation pattern in a direction away from the user of the electronic device.

19. An electronic device comprising:
  control means for directing multiple antennas disposed on or within the electronic device to dynamically adjust a cumulative radiation in a manner that reduces wireless energy exposure to a user of the electronic device,
  wherein the wireless power reception apparatus is configured to wirelessly receive power from a wireless power delivery system in a wireless power delivery environment.

20. The electronic device of claim 19, wherein the control means are further configured for:
  detecting one or more full or partial blockages of radiation patterns associated with the multiple antennas,
  wherein each of the multiple antennas have a corresponding radiation pattern that is adjustable over amplitude and phase by the control system,
  wherein the radiation patterns collectively comprise the cumulative radiation pattern, and
  wherein the cumulative radiation pattern is adjusted based on the one or more full or partial blockages.

* * * * *

UNITED STATES PATENT AND TRADEMARK OFFICE
CERTIFICATE OF CORRECTION

PATENT NO. : 10,651,659 B2
APPLICATION NO. : 16/243611
DATED : May 12, 2020
INVENTOR(S) : Hatem Ibrahim Zeine et al.

Page 1 of 1

It is certified that error appears in the above-identified patent and that said Letters Patent is hereby corrected as shown below:

In the Claims

Column 24, Claim 2, Line 2, delete "patterns" and insert --pattern--

Signed and Sealed this
Eighth Day of December, 2020

Andrei Iancu
*Director of the United States Patent and Trademark Office*